(12) United States Patent
Asai

(10) Patent No.: US 11,110,253 B2
(45) Date of Patent: Sep. 7, 2021

(54) CATHETER ASSEMBLY

(71) Applicant: TERUMO KABUSHIKI KAISHA, Tokyo (JP)

(72) Inventor: Toshiya Asai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 61 days.

(21) Appl. No.: 16/103,526

(22) Filed: Aug. 14, 2018

(65) Prior Publication Data

US 2018/0369540 A1 Dec. 27, 2018

Related U.S. Application Data

(63) Continuation of application No. PCT/JP2016/079206, filed on Oct. 3, 2016.

(30) Foreign Application Priority Data

Feb. 18, 2016 (JP) .............................. JP2016-028781

(51) Int. Cl.
*A61M 25/06* (2006.01)
*A61M 25/00* (2006.01)
(Continued)

(52) U.S. Cl.
CPC .... *A61M 25/0606* (2013.01); *A61M 25/0045* (2013.01); *A61M 25/0097* (2013.01);
(Continued)

(58) Field of Classification Search
CPC .......... A61M 25/0606; A61M 25/0612; A61M 25/0631; A61M 25/09041;
(Continued)

(56) References Cited

U.S. PATENT DOCUMENTS 5,403,283 A 4/1995 Luther
5,599,305 A * 2/1997 Hermann ......... A61B 17/12036
604/200

(Continued)

FOREIGN PATENT DOCUMENTS

CN 1703254 A 11/2005
CN 105102053 A 11/2015
(Continued)

OTHER PUBLICATIONS

English translation of Ishida (WO2014199697).*
(Continued)

*Primary Examiner* — Amber R Stiles
*Assistant Examiner* — Alexandra Lalonde
(74) *Attorney, Agent, or Firm* — Foley & Lardner LLP

(57) ABSTRACT

A catheter assembly includes: a catheter; a catheter hub connected to the catheter; an inner needle removably disposed in the catheter; a needle hub connected to the inner needle; and a deflection suppressing member that suppresses deflection of the inner needle by supporting the inner needle via the catheter at a location distal of the catheter hub. The deflection suppressing member is supported so as to be movable relative to the needle hub in an axial direction.

19 Claims, 18 Drawing Sheets

(51) Int. Cl.
    A61M 25/09    (2006.01)
    A61M 25/02    (2006.01)
(52) U.S. Cl.
    CPC .. *A61M 25/0631* (2013.01); *A61M 25/09041*
        (2013.01); *A61M 2025/006* (2013.01); *A61M
        2025/0046* (2013.01); *A61M 2025/0062*
        (2013.01); *A61M 2025/0293* (2013.01); *A61M
        2025/0687* (2013.01)
(58) Field of Classification Search
    CPC ...... A61M 25/0045; A61M 2005/1585; A61M
            2025/0046; A61M 2025/0048; A61M
            25/0152; A61M 25/06; A61M 25/0618;
            A61M 25/0625; A61M 25/0637; A61M
            25/0643; A61M 25/065; A61M 25/0662;
            A61M 25/0668; A61M 25/0693; A61M
            2025/0675; A61M 2025/0681; A61M
            2025/0687; A61M 25/0097; A61M
                                        2025/006
    See application file for complete search history.

(56)            References Cited

U.S. PATENT DOCUMENTS 8,043,268   B1    10/2011   Marks
    2009/0143737 A1 *  6/2009   Kobayashi ............ A61M 5/158
                                                        604/164.08
    2012/0010577 A1 *  1/2012   Liska ................ A61M 25/0606
                                                        604/272
    2013/0023826 A1 *  1/2013   Ishida .................. A61M 5/158
                                                        604/165.02

FOREIGN PATENT DOCUMENTS

CN          105120938  A       12/2015
    CN          105246536  A        1/2016
    EP          2 229 975  B1      11/2013
    JP          H10-503094 A        3/1998
    JP          2003-180833 A       7/2003
    JP          4294929    B2       7/2009
    WO          WO-2011/118643 A1   9/2011
    WO          WO-2014/133617 A1   9/2014
    WO          WO-2014199697 A1 * 12/2014 ........ A61M 25/0606
    WO          WO-2015/082551 A1   6/2015
    WO          WO-2015/115315 A1   8/2015
    WO          WO-2016/020923 A2   2/2016
    WO          WO-2016020923 A2 *  2/2016 ........ A61M 25/0606

OTHER PUBLICATIONS

Extended European Search Report dated Oct. 21, 2019 in corresponding European Application No. 16890619.6.
Translation of the International Search Report in corresponding application No. PCT/JP2016/079206.
Translation of the Written Opinion of the International Searching Authority in corresponding application No. PCT/JP2016/079206.
International Search Report with English language translation and Written Opinion issued in International Application No. PCT/JP2016/079206 dated Dec. 20, 2016.
Office Action and Search Report dated Aug. 19, 2020 in corresponding Chinese Patent Application No. 201680082073.7.
Office Action dated May 12, 2020 in corresponding Japanese Patent Application No. 2017-567944.

* cited by examiner

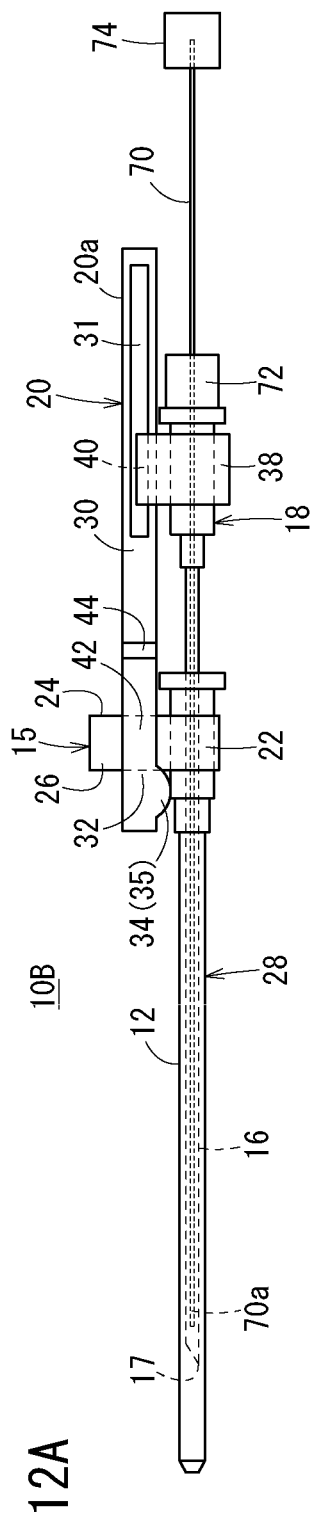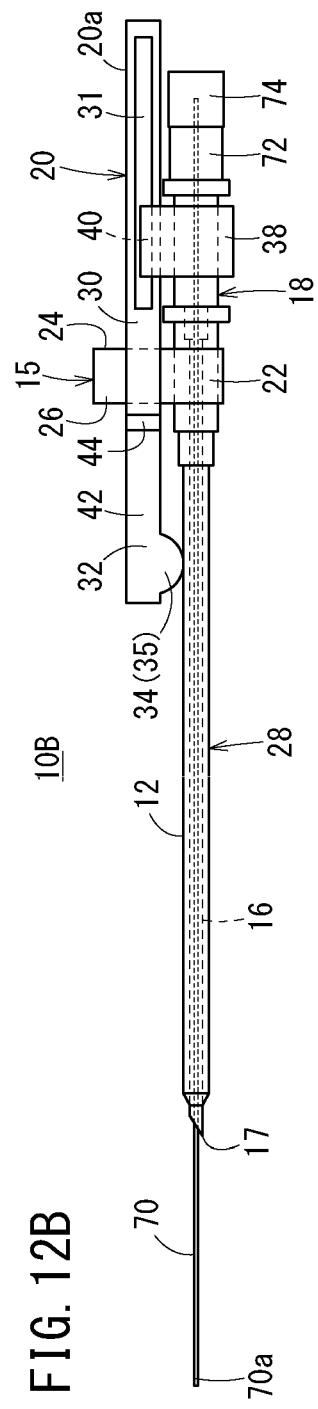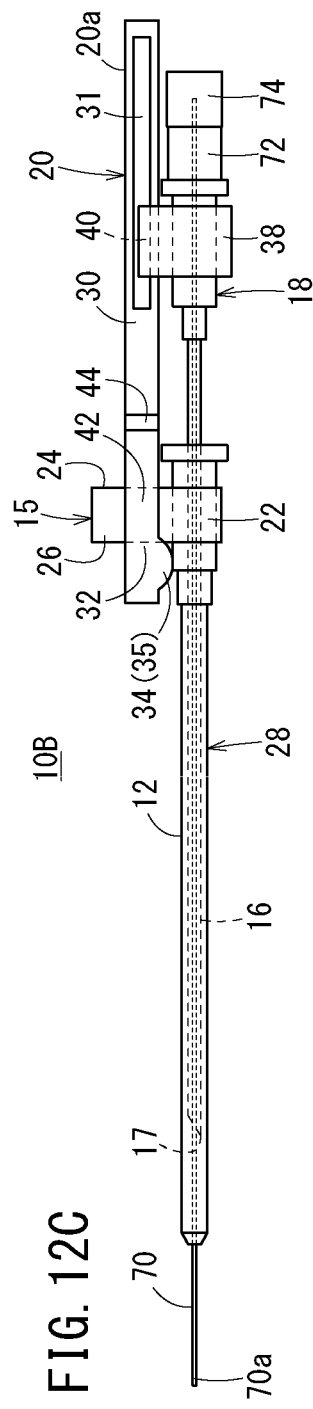
FIG. 12A
FIG. 12B
FIG. 12C

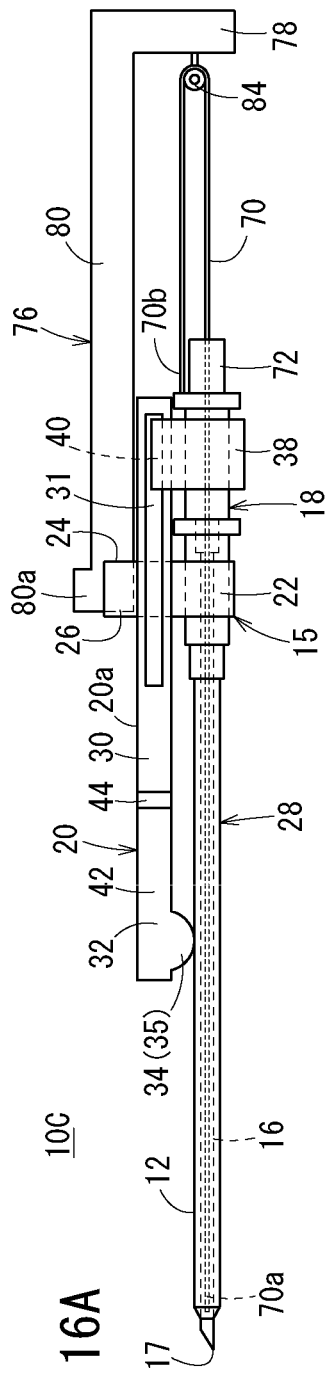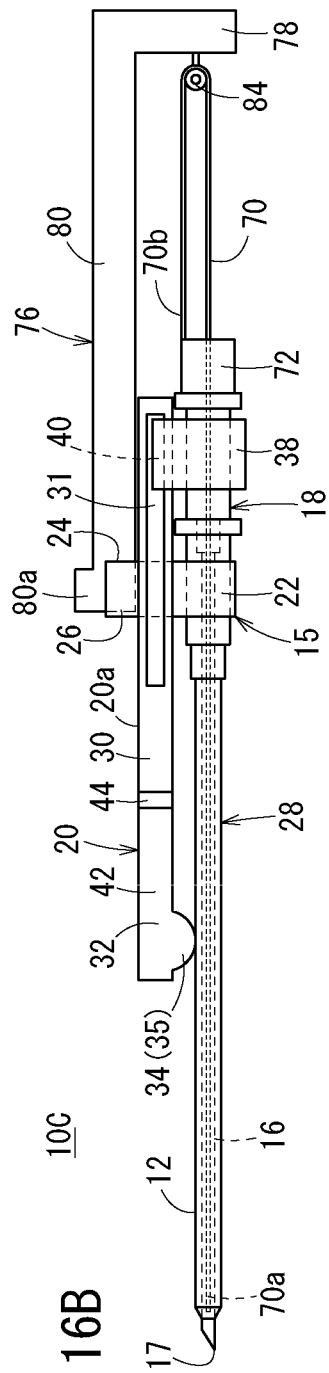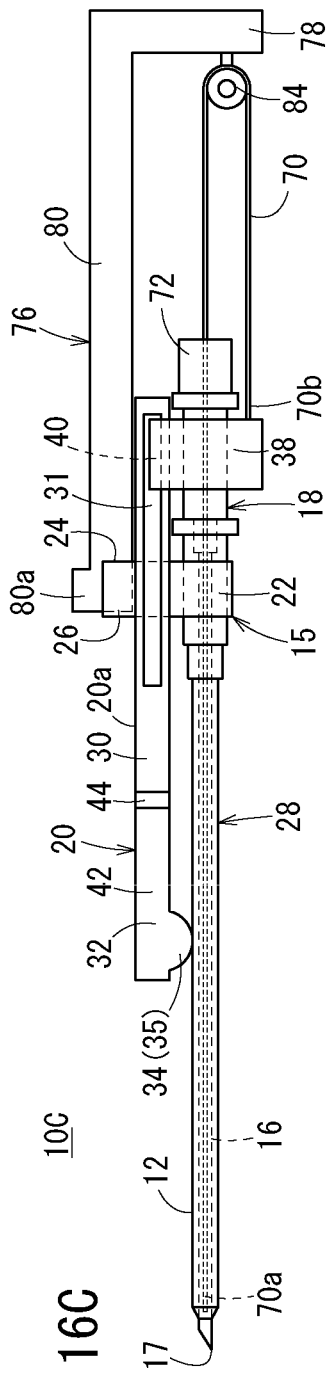

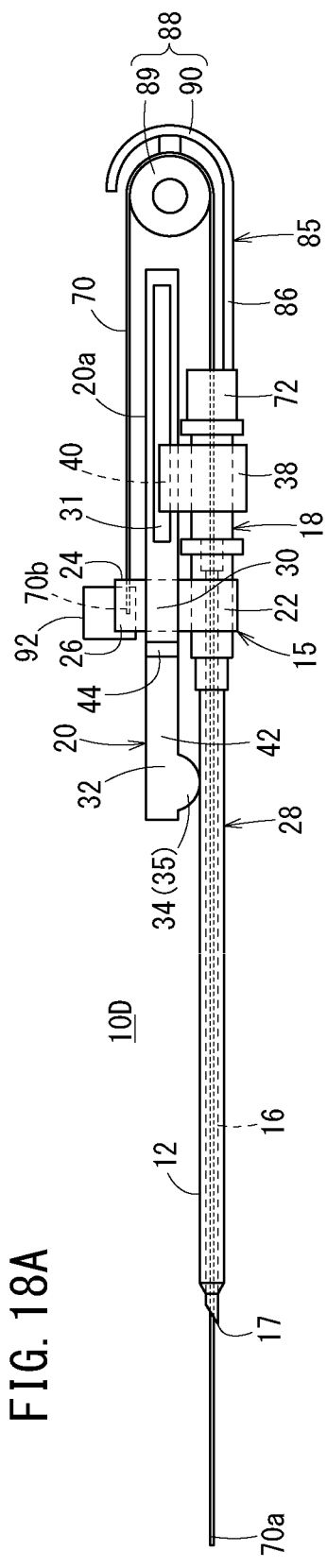

CATHETER ASSEMBLY

CROSS-REFERENCE TO RELATED APPLICATIONS

This is a bypass continuation of PCT Appl. No. PCT/JP2016/079206 filed on Oct. 3, 2016, which claims priority to Japanese Appl. No. 2016-028781, filed on Feb. 18, 2016. The contents of these application are hereby incorporated by reference in their entireties.

BACKGROUND

The present disclosure relates to a catheter assembly for indwelling by puncturing a blood vessel for performing infusion to a patient, for example.

Conventionally, a practitioner uses a catheter assembly, for example, when performing infusion to a patient. A catheter assembly of this type includes a hollow catheter, a catheter hub fixed to a proximal end of the catheter, an inner needle inserted into the catheter and having a sharp needle point at its distal end, and a needle hub attached to the proximal end of the inner needle (refer to JP 4294929 B, for example).

When the practitioner performs infusion to a patient using a catheter assembly, the practitioner performs puncture into the blood vessel of the patient with the catheter together with the inner needle. After the puncture, the practitioner withdraws the inner needle from the catheter while maintaining the state in which the patient's blood vessel is punctured with the catheter. Next, the practitioner connects a connector provided at an end portion of an infusion tube to the proximal end of the catheter hub. Thereafter, the practitioner supplies an infusion agent into the blood vessel of the patient via the infusion tube, the catheter hub, and the catheter.

SUMMARY

Such a catheter assembly has a problem of having difficulty in performing puncture operation due to deflection of the inner needle and the catheter during the puncture operation. The length of each of the inner needle and the catheter is set relatively long, particularly when the catheter assembly is configured as a central venous catheter, PICC, midline catheter, long peripheral venous catheter, or the like. This would make the problem of deflection of the inner needle and catheter more prominent.

Certain embodiments of the present disclosure have been made in view of this problem and aims to provide a catheter assembly capable of suppressing deflection of an inner needle during a puncture operation.

According to one embodiment of the present disclosure, a catheter assembly includes a catheter, a catheter hub connected to the catheter, an inner needle removably inserted into the catheter, a needle hub connected to the inner needle, and a deflection suppressing member that suppresses deflection of the inner needle by supporting the inner needle via the catheter at a location distal of the catheter hub, in which the deflection suppressing member is supported so as to be movable relative to the needle hub in the axial direction.

With the catheter assembly according the above configuration, the catheter and the inner needle may be supported by the deflection suppressing member during a puncture operation, leading to suppression of the deflection of the inner needle. This makes it possible to perform puncture operation smoothly. Furthermore, it is possible, at the time of puncturing, to move the inner needle and the catheter in the distal end direction while holding the position of the deflection suppressing member. This makes it possible to puncture while supporting the catheter and the inner needle by the deflection suppressing member without causing interference between the deflection suppressing member and the skin of the patient.

In the above-described catheter assembly, the deflection suppressing member may include, at the distal end thereof, a support portion coming in contact with the catheter, and the support portion may be configured to be movable relative to the catheter while maintaining a state of being in contact with the catheter.

In the above-described catheter assembly, the needle hub may have a guide projection, the deflection suppressing member may have a groove portion configured to engage with the guide projection of the needle hub, and a length of the groove portion may be longer than ½ of an overall length of the catheter.

The above-described catheter assembly may further include a catheter operating portion provided on the catheter hub, in which the deflection suppressing member may include a slit permitting relative movement of the catheter operating portion in the axial direction, and the catheter operating portion may protrude from a side opposite to the catheter hub of the deflection suppressing member via the slit in the deflection suppressing member.

With this configuration, when performing advancing operation of the catheter with respect to the inner needle, the user can easily perform the advancing operation of the catheter by operating the catheter operating portion protruding from the deflection suppressing member. In addition, because the slit is provided in the deflection suppressing member, the advancing operation can be performed without hindrance of the advancing movement of the catheter by the deflection suppressing member.

In the catheter assembly, the deflection suppressing member may include: a base portion supported by the needle hub and extending along the axial direction of the inner needle; and a distal end forming portion extending from the base portion in a distal end direction and extending from the slit and enabling detachment of the catheter operating portion from the slit.

With this configuration, the catheter operating portion can be detached from the deflection suppressing member after completion of the advancing operation of the catheter, making it possible to remove the inner needle from the catheter without a problem.

In the above catheter assembly, the distal end forming portion may include two arms that close a distal end of the slit in an initial state, and at least one arm of the two arms may be movable with respect to the base portion.

With this configuration, a detachment mechanism can be constructed with a simple configuration.

In the above catheter assembly, the at least one arm may be pivotable with respect to the base portion via a hinge portion.

With this configuration, it is possible to easily form a gap through which the catheter operating portion can pass at the distal end portion of the deflection suppressing member by moving the arm with the hinge portion as a fulcrum.

In the above catheter assembly, the at least one arm may be detachable from the base portion.

With this configuration, the catheter operating portion can easily be brought into a detachable state from the deflection suppressing member by removing the arm from the base portion.

In the above catheter assembly, the catheter operating portion may include an engaging portion configured to engage with the deflection suppressing member so as to suppress deflection of the deflection suppressing member.

With this configuration, the deflection of the deflection suppressing member itself is suppressed, making it possible to further effectively suppress the deflection of the catheter and the inner needle supported by the deflection suppressing member.

In the catheter assembly described above, the deflection suppressing member may include a support portion that is in contact with or in proximity to an outer peripheral surface of the catheter and that surrounds at least half of the outer peripheral surface of the catheter in a circumferential direction.

With this configuration, it is possible to suppress deflection of the inner needle and the catheter in all directions around the catheter.

In the catheter assembly described above, a friction reduction member for reducing frictional resistance between the support portion and the catheter may be provided on an inner peripheral portion of the support portion.

With this configuration, it is possible to suppress peeling of a coating due to the contact between the catheter and the support portion even in a case in which the coating for reducing puncture resistance is applied to the outer peripheral surface of the catheter.

In the above catheter assembly, the friction reduction member may be a gel material or a rolling element coming in contact with the catheter.

With this configuration, it is possible to effectively reduce frictional resistance between the holding portion and the catheter.

In the above catheter assembly, the inner needle may be a hollow member having an inner cavity, and the catheter assembly may further include a guide wire inserted through the inner cavity so as to be movable relative to the inner needle in the axial direction.

With this configuration, in execution of the advancing operation for inserting the catheter into the blood vessel for a predetermined length, it is possible to execute the advancing operation smoothly by advancing the catheter along the guide wire inserted in the blood vessel beforehand.

The above-described catheter assembly may further include: a wire operating portion that supports the guide wire; and a catheter operating portion provided on the catheter hub, in which the catheter operating portion may further include an operating element protruding from the side opposite to the catheter hub of the deflection suppressing member, and the distal end portion of the wire operating portion may be in contact with or in proximity to the operating element of the catheter operating portion in an initial state of the catheter assembly.

With this configuration, the distal end portion of the wire operating portion can be operated with the same hand as the hand operating the operating element of the catheter operating portion, leading to excellent operability.

With the catheter assembly according to certain embodiments of the present disclosure, it is possible to suppress deflection of the inner needle at the time of puncture operation.

BRIEF DESCRIPTION OF THE DRAWINGS

FIG. 12A is a second diagram illustrating a method of using the catheter assembly according to the second embodiment. FIG. 12B is a third diagram illustrating a method of using the catheter assembly according to the second embodiment. FIG. 12C is a fourth diagram illustrating a method of using the catheter assembly according to the second embodiment.

FIG. 16A is a side view of a first modification of the catheter assembly according to the third embodiment. FIG. 16B is a side view of a second modification of the catheter assembly according to the third embodiment. FIG. 16C is a side view of a third modification of the catheter assembly according to the third embodiment.

FIG. 18A is a second diagram illustrating a method of using the catheter assembly according to the fourth embodiment. FIG. 18B is a third diagram illustrating a method of using the catheter assembly according to the fourth embodiment.

DETAILED DESCRIPTION

Hereinafter, preferred embodiments of a catheter assembly according to the present disclosure will be described with reference to the accompanying drawings.

First Embodiment

Figure 1A:
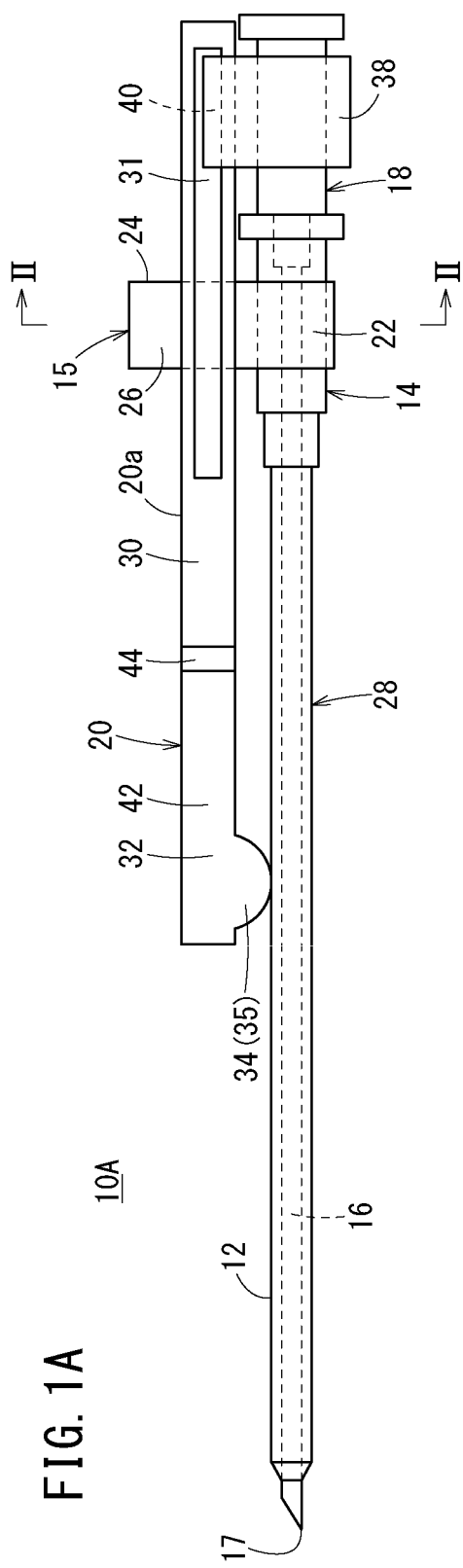
FIG. 1A is a side view of a catheter assembly according to a first embodiment.
Figure 1B:
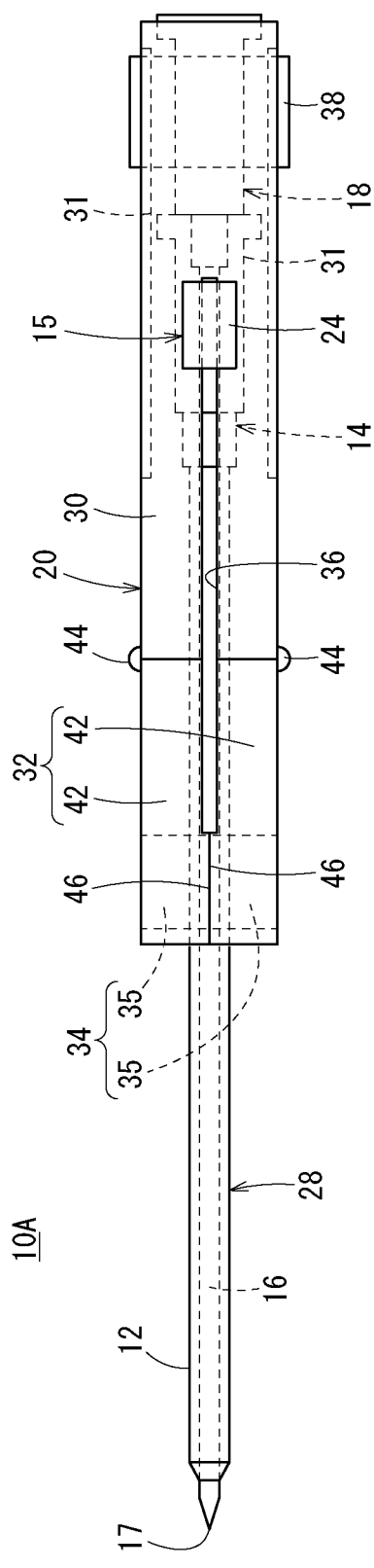
FIG. 1B is a plan view of the catheter assembly according to the first embodiment.

A catheter assembly 10A according to a first embodiment illustrated in FIGS. 1A and 1B is used for administering an infusion agent (medical solution) to a patient, for example. The catheter assembly 10A may be configured as a peripheral venous catheter. The catheter assembly 10A may also be configured as a catheter that is longer than the peripheral venous catheter, such as a central venous catheter, a PICC, or a midline catheter. Furthermore, the catheter assembly 10A is not limited to a venous catheter, and may be configured as an arterial catheter such as a peripheral artery catheter.

The catheter assembly 10A includes a catheter 12, a catheter hub 14 connected to the proximal end side of the catheter 12, a catheter operating portion 15 attached to the catheter hub 14, an inner needle 16 removably inserted into the catheter 12, a needle hub 18 connected to the inner needle 16, and a deflection suppressing member 20 for suppressing deflection of the inner needle 16 during puncture.

In the use of the catheter assembly 10A, the needle hub 18 is grasped by a user (a doctor, a nurse, etc.) for operation, so as to allow its distal end portion to be punctured into the blood vessel 50 of the patient. In an initial state before use (before puncturing the patient), the catheter assembly 10A has a double-tube structure in which the inner needle 16 is inserted through the catheter 12, with the inner needle 16 protruding by a predetermined length from the distal end of the catheter 12.

The catheter assembly 10A in the initial state is formed by combining a double-tube structure of the catheter 12 and the inner needle 16, the catheter hub 14, the needle hub 18, and the deflection suppressing member 20 to constitute one assembly and can be handled integrally.

The catheter 12 is a flexible thin tubular member formed to have a predetermined length. As the constituent material of the catheter 12, a resin material, particularly, a soft resin material is suitable. The length of the catheter 12 is not particularly limited, and is appropriately set in accordance with the use, various conditions, or the like. Examples of the length of the catheter 12 are about 20 to 500 mm, about 30 to 400 mm, or about 100 to 300 mm.

The catheter hub 14 is a hollow member having an inner cavity communicating with the inner cavity of the catheter 12, and is formed thicker than the catheter 12. The catheter hub 14 is liquid-tightly connected and fixed to the proximal end portion of the catheter 12. Example of a constituent material of the catheter hub 14 is a hard resin such as polypropylene.

The catheter operating portion 15 is an operating portion for performing an advancing operation of the catheter 12, and is attached to the catheter hub 14. In FIG. 1A, the catheter operating portion 15 includes: a fixed base portion 22 fixed to the catheter hub 14; and an extending portion 24 extending upward from the fixed base portion 22. An operating element 26 (finger grip portion) for the user to apply own fingers is provided at an extending end of the extending portion 24.

The catheter operating portion 15 penetrates a slit 36 (refer to FIG. 1B), described below, that is formed in the deflection suppressing member 20. The above-described operating element 26 protrudes from an upper surface 20a of the deflection suppressing member 20. The user can operate the catheter hub 14 in the axial direction by touching and then grasping or pressing the portion (operating element 26) protruding from the deflection suppressing member 20, on the catheter operating portion 15.

Figure 2:
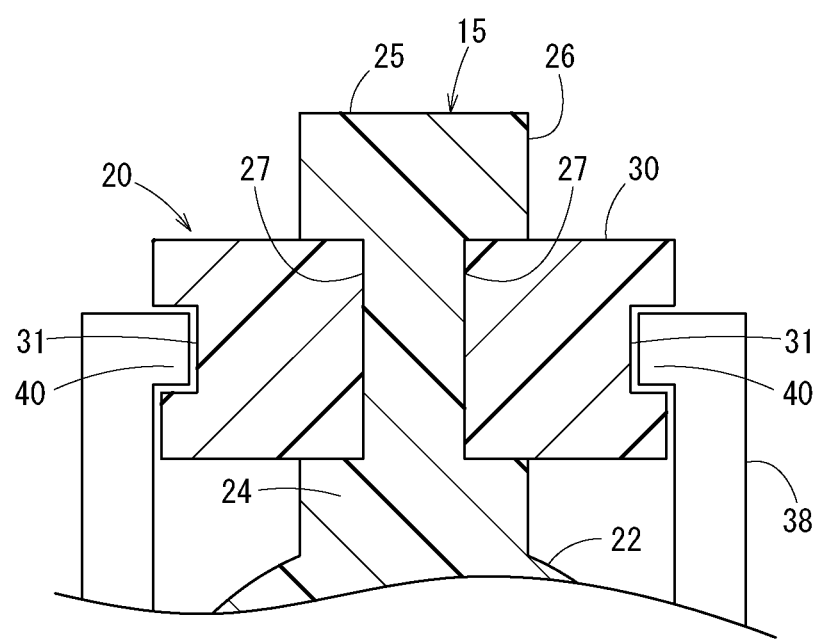
FIG. 2 is a cross-sectional view taken along line II-II in FIG. 1A.

As illustrated in FIG. 2, an engaging groove 27 (engaging portion) to slidably engage with the deflection suppressing member 20 in an axial direction is formed on the extending portion 24, more toward the fixed base portion 22 side than the operating element 26.

Note that the catheter operating portion 15 may be configured to be removable from the catheter hub 14. Alternatively, the catheter operating portion 15 may be formed integrally with the catheter hub 14. Hereinafter, a member including the catheter 12, the catheter hub 14, and the catheter operating portion 15 will be referred to as a "catheter member 28".

In FIGS. 1A and 1B, the inner needle 16 is a hollow elongated member having a sharp needle point 17 at its distal end and having rigidity capable of puncturing patient's skin 48. In the initial state of the catheter assembly 10A, the needle point 17 of the inner needle 16 protrudes from a distal end opening of the catheter 12 by a predetermined length. In addition, in the initial state, a middle site in the longitudinal direction of the inner needle 16 is inserted into the catheter hub 14, and the proximal end side of the inner needle 16 is held by the needle hub 18.

Examples of a constituent material of the inner needle 16 include: a metal material such as stainless steel; a hard resin; a ceramics material, or the like. The inner needle 16 may have a solid structure.

Next, the deflection suppressing member 20 will be described. The deflection suppressing member 20 supports the inner needle 16 on more distal end side than the catheter hub 14 via the catheter 12 and is supported so as to be displaceable relative to the needle hub 18 in the axial direction.

Specifically, the deflection suppressing member 20 includes: a base portion 30 extending along the axial direction of the inner needle 16; a distal end forming portion 32 extending from the distal end of the base portion 30 in the distal end direction; a support portion 34 provided at the distal end forming portion 32 and coming in contact with or in the proximity to the outer peripheral surface of the catheter 12; and a slit 36 (refer to FIGS. 1B and 3) extending along the longitudinal direction of the deflection suppressing member 20.

The base portion 30 is formed in a plate shape and is slidably supported in the axial direction by a slide support body 38 fixed to the needle hub 18. A guide groove 31 (groove portion) extending in the longitudinal direction of the base portion 30 is formed on each of side surfaces on both sides in the left-right direction (width direction) of the base portion 30. A portion (proximal end side portion) of the slit 36 is formed in the base portion 30. The slit 36 penetrates in the thickness direction of the deflection suppressing member 20.

As illustrated in FIG. 2, a pair of guide projections 40 protruding inward in the left-right direction is provided on the upper portion of the slide support body 38. The guide projection 40 is inserted into the guide groove 31. This configuration enables the deflection suppressing member 20 to move relative to the needle hub 18 smoothly in the axial direction. It is desirable that the relationship between a length (L1) of the guide groove 31 and an overall length (L2) of the catheter 12 be L1>L2/2. With this configuration, the deflection suppressing member 20 can support more distal end side of the catheter 12 than a middle portion (center portion in the longitudinal direction), and the deflection suppressing member 20 can move to a proximal side of the proximal end portion of the catheter 12 as necessary.

As illustrated in FIG. 1B, the distal end forming portion 32 includes two arms 42 juxtaposed in an initial state and is configured to be changeable from a closed state to an open state permitting passage of the catheter operating portion 15. In the present embodiment, each of the arms 42 is connected to the distal end portion of the base portion 30 via a hinge portion 44, and is pivotable with respect to the base portion 30 with the hinge portion 44 as a fulcrum.

Specifically, each of the arms 42 is pivotable in a direction away from each other about an axis extending in the thickness direction of the deflection suppressing member 20. The hinge portion 44 may be a thin portion integrally formed with the base portion 30 and the arm 42, or may be a fitting structure of an axial portion and a hole portion.

Figure 3:
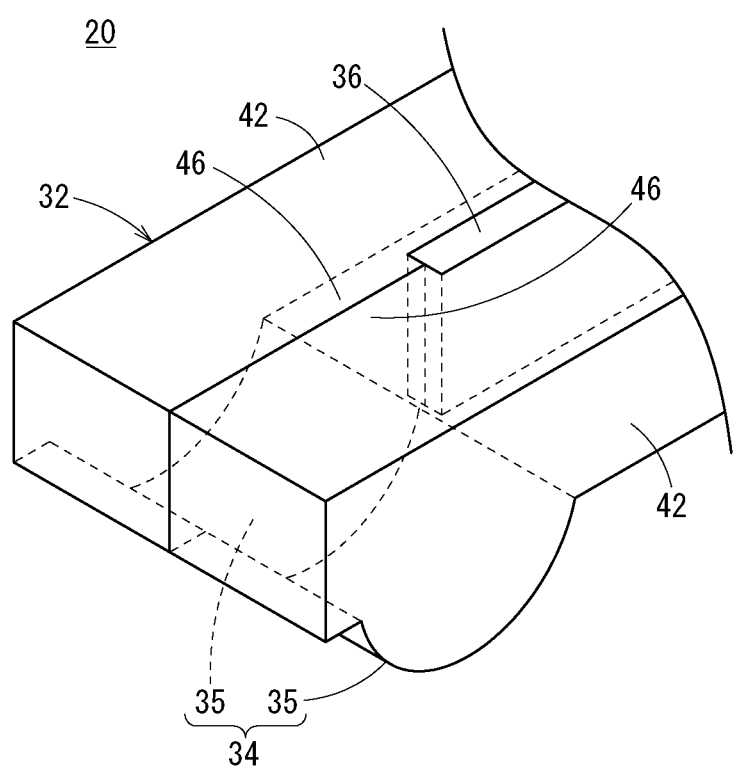
FIG. 3 is a perspective view of a distal end portion of a deflection suppressing member of the catheter assembly according to the first embodiment.

As illustrated in FIG. 3, a protrusion 46 protruding slightly inward is provided on the inner side of the distal end portion of each of the arms 42. In the initial state, the protrusions 46 are brought into contact with each other, so as to close the distal end forming portion 32. A gap is formed between the two arms 42, on more proximal end side than the protrusion 46, and this gap constitutes the other portion (the distal end side portion) of the slit 36.

The support portion 34 protrudes toward the catheter 12 side, on a side (lower surface in FIG. 1A) of the deflection suppressing member 20 facing the catheter 12. In the initial state, the support portion 34 may be in contact with the outer peripheral surface of the catheter 12 or may be slightly separated from the outer peripheral surface of the catheter 12. As illustrated in FIG. 3, the support portion 34 is formed with two support elements 35. One support element 35 is provided on one arm 42. The other support element 35 is provided on the other arm 42.

Next, functions and effects of the catheter assembly 10A configured as described above will be described.

In the use of the catheter assembly 10A, a user (a doctor, a nurse, or the like) serving as a practitioner grasps the needle hub 18 (and its peripheral members as necessary) of the catheter assembly 10A in the initial state illustrated in FIGS. 1A and 1B. Then, as illustrated in FIG. 4, the user punctures the patient's skin 48 with the catheter 12 and the inner needle 16 toward a patient's blood vessel 50.

During this puncture, deflection of the inner needle 16 is suppressed by the deflection suppressing member 20. That is, the support portion 34 holds the catheter 12 to enable the inner needle 16 to be supported by the deflection suppressing member 20 via the catheter 12 even when the inner needle 16 is going to deflect toward the side opposite to the skin 48 at the time of puncturing. This configuration suppresses the deflection of the inner needle 16 at the time of puncture, enabling stable puncturing. At this time, the support portion 34 is in contact with the middle portion of the catheter 12.

Figure 4:
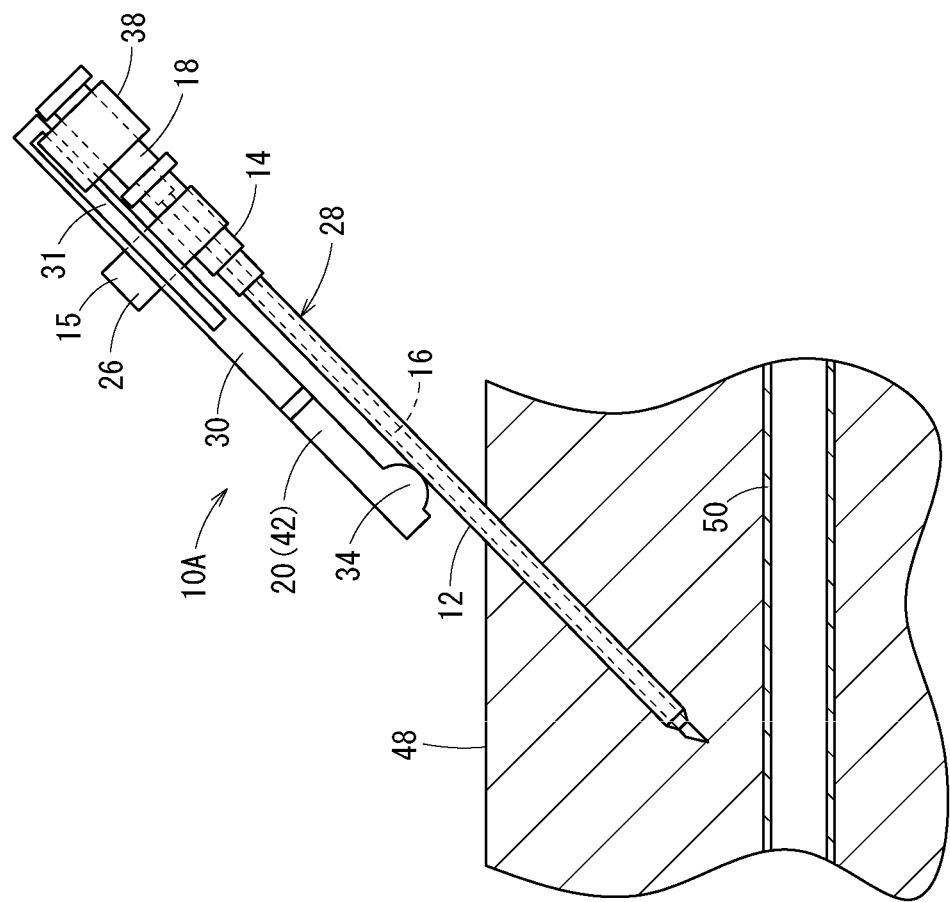
FIG. 4 is a first diagram illustrating a method of using the catheter assembly according to the first embodiment.
Figure 5:
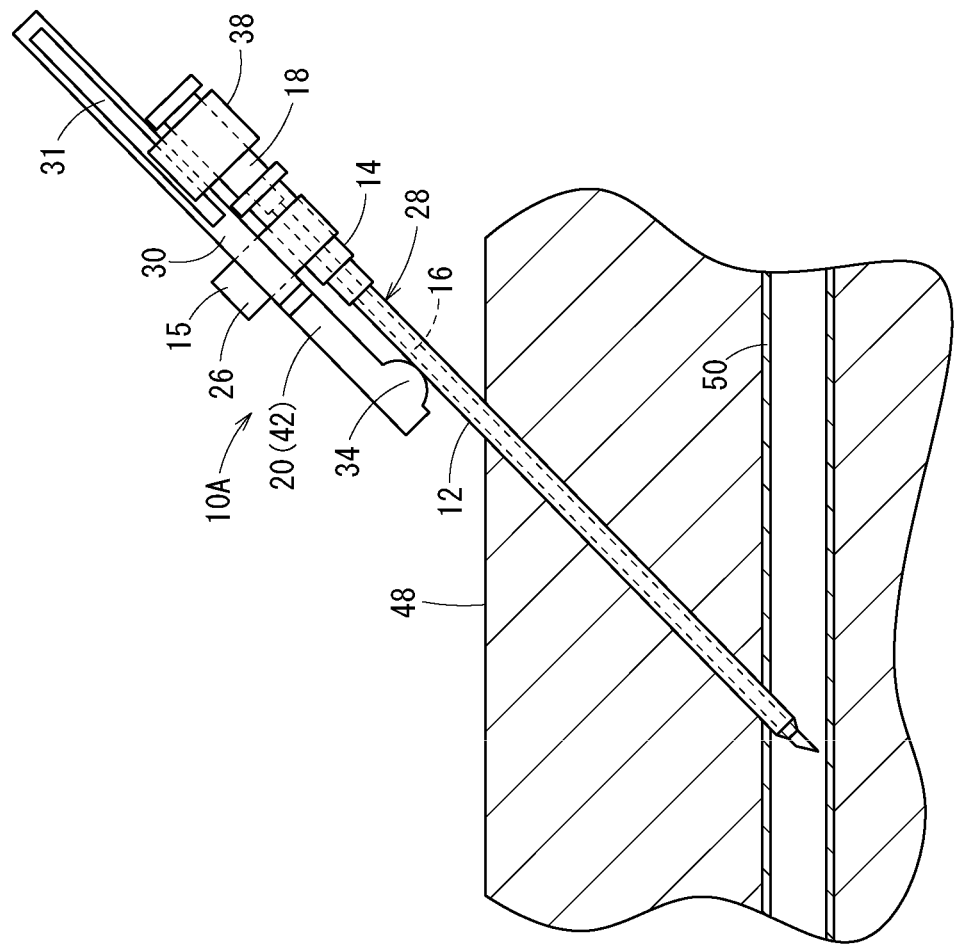
FIG. 5 is a second diagram illustrating a method of using the catheter assembly according to the first embodiment.

While the inner needle 16 and the catheter 12 have not reached the blood vessel 50 in the state of FIG. 4, if the entire catheter assembly 10A is advanced as it is in order to allow the inner needle 16 and the catheter 12 to reach the blood vessel 50, the deflection suppressing member 20 would come into contact with the skin 48. To avoid this, as illustrated in FIG. 5, the user advances the members (the inner needle 16, the catheter 12, or the like) other than the deflection suppressing member 20 in the catheter assembly 10A while holding the position of the deflection suppressing member 20, thereby puncturing the blood vessel 50 with the distal ends of the inner needle 16 and the catheter 12. At this time, the catheter operating portion 15 advances in the slit 36 (refer to FIG. 1B). At this time, the support portion 34 retreats with respect to the catheter 12 while maintaining the state of being in contact with the catheter 12.

At the time of this advancing operation, deflection of the inner needle 16 is also suppressed by the deflection suppressing member 20. That is, while the catheter assembly 10A moves from the state illustrated in FIG. 4 to the state illustrated in FIG. 5, the inner needle 16 is supported, via the catheter 12, by the deflection suppressing member 20 moving relative to the needle hub 18 in the proximal end direction. Consequently, with the use of the catheter assembly 10A, the deflection of the inner needle 16 at the time of puncturing is suppressed to enable stable puncturing during the period from the start of the puncture into the skin 48 to the completion of the puncture into the blood vessel 50.

Figure 6:
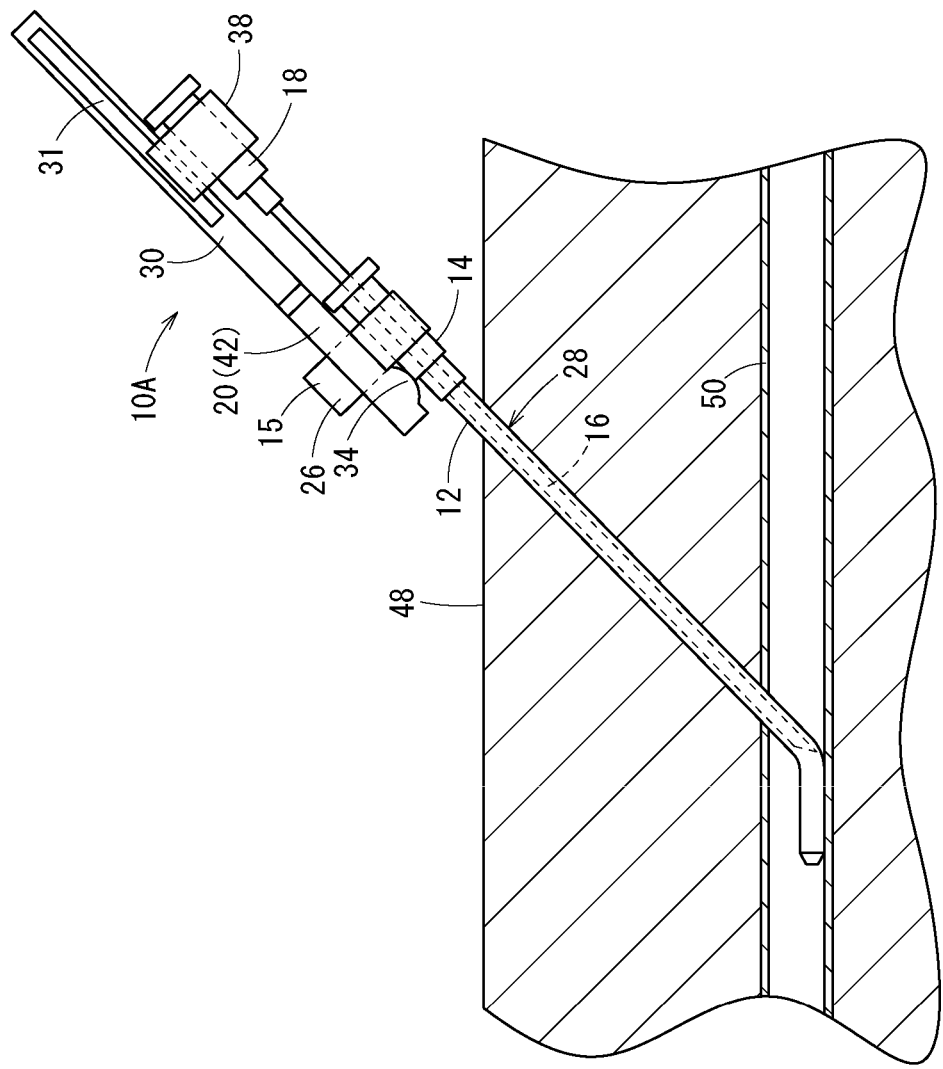
FIG. 6 is a third diagram illustrating a method of using the catheter assembly according to the first embodiment.

After puncturing the blood vessel 50, the user hooks own finger to the catheter operating portion 15 protruding upward from the deflection suppressing member 20 and pushes the catheter operating portion 15 in the distal end direction while holding the position of the deflection suppressing member 20. Then, as illustrated in FIG. 6, the catheter hub 14 and the catheter 12 connected to the catheter operating portion 15 move in the distal end direction with respect to the inner needle 16 and the needle hub 18, increasing the insertion length of the catheter 12 into the blood vessel 50.

Once the user has inserted the catheter 12 by a predetermined length into the blood vessel 50, then the user pulls the needle hub 18 in the proximal end direction with the position of the catheter member 28 held. Then, the inner needle 16 moves in the proximal end direction within the catheter member 28, and eventually the inner needle 16 is completely removed from the catheter member 28. As a result, the catheter member 28 alone among the catheter assembly 10A is indwelled on the patient side.

Figure 7A:
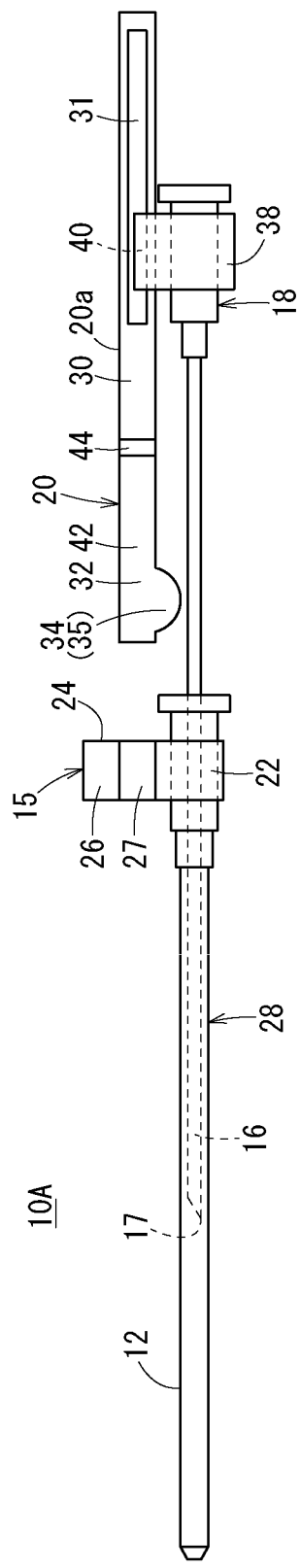
FIG. 7A is a fourth view (side view) illustrating a method of using the catheter assembly according to the first embodiment.
Figure 7B:
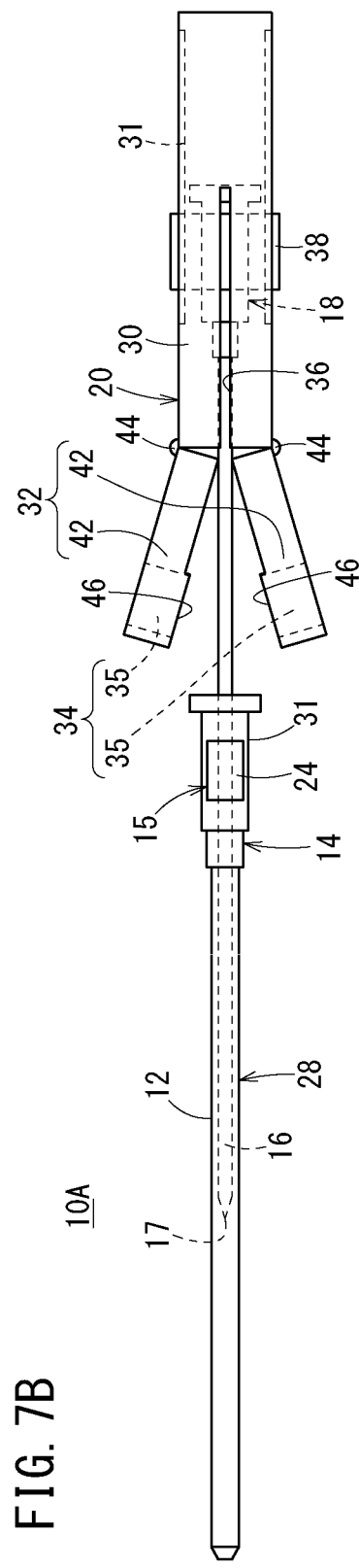
FIG. 7B is a plan view of the catheter assembly in the state of FIG. 7A.

In this manner, during advancing operation of the catheter 12 with respect to the inner needle 16 in order to insert the catheter 12 by a predetermined length into the blood vessel 50, or while pulling the needle hub 18 in the proximal end direction in order to remove the inner needle 16 from the catheter 12, the catheter operating portion 15 is detached from the deflection suppressing member 20 in the distal end direction as illustrated in FIGS. 7A and 7B. Specifically, together with the relative movement of the deflection suppressing member 20 and the catheter operating portion 15 in the axial direction, the catheter operating portion 15 pushes the two arms 42 (proximal ends of the protrusions 46) in the distal end direction. With this pushing force, the two arms 42 expand in the left-right direction, permitting passage of the catheter operating portion 15.

In this manner, the deflection suppressing member 20 suppresses the deflection of the inner needle 16 at the time of puncture by supporting the inner needle 16 until completion of the puncture into the blood vessel 50 during the puncture operation. In addition, after the puncture, the deflection suppressing member 20 opens the distal end forming portion 32 (two arms 42 in the present embodiment) to prevent interference with the catheter operating portion 15.

After withdrawing the inner needle 16 from the catheter member 28 as described above, the user fixes the catheter hub 14 to the patient with a dressing material, a tape, or the like. Then, the user connects a connector of an infusion tube (not illustrated) to the proximal end side of the catheter hub 14, and supplies an infusion agent (medical solution) to the patient from the infusion tube. Note that, in a case in which the catheter operating portion 15 is detachable from the catheter hub 14, the catheter operating portion 15 may first be removed from the catheter hub 14 and then the catheter hub 14 may be fixed to the patient with a dressing material or the like.

As described above, with the catheter assembly 10A according to the first embodiment, the inner needle 16 is supported by the deflection suppressing member 20 at the time of puncture, leading to suppression of the deflection of the inner needle 16 at the time of puncture, enabling execution of stable puncture. Therefore, the puncture operation can be performed smoothly. Furthermore, it is possible at the time of puncturing to move the inner needle 16 and the catheter 12 in the distal end direction while holding the position of the deflection suppressing member 20. This makes it possible to puncture while supporting the inner needle 16 by the deflection suppressing member 20 without causing interference between the deflection suppressing member 20 and the skin 48 of the patient.

With this catheter assembly 10A, when advancing the catheter 12 with respect to the inner needle 16, the user can easily perform the advancing operation of the catheter 12 by operating the catheter operating portion 15 protruding from the deflection suppressing member 20. In addition, because the slit 36 (refer to FIG. 1B) is provided in the deflection suppressing member 20, the advancing operation can be performed without hindrance of the advancing movement of the catheter 12 by the deflection suppressing member 20.

In the catheter assembly 10A, the deflection suppressing member 20 includes a distal end forming portion 32 that enables the catheter operating portion 15 to be detached from the slit 36. With this configuration, the catheter operating portion 15 can be detached from the deflection suppressing member 20 after completion of the advancing operation of the catheter 12, making it possible to remove the inner needle 16 from the catheter 12 without a problem.

In the catheter assembly 10A, the arm 42 is coupled to the base portion 30 via a hinge portion 44. With this configuration, it is possible to easily form a gap through which the catheter operating portion 15 can pass at the distal end portion of the deflection suppressing member 20 by moving the arm 42 with the hinge portion 44 as a fulcrum. In addition, because the two arms 42 are automatically expanded together with advance of the catheter operating portion 15, there is no need to perform an independent spreading operation, leading to excellent operability.

The catheter assembly 10A includes the engaging groove 27 (engaging portion) to engage with the deflection suppressing member 20, leading to suppression of deflection of the deflection suppressing member 20 itself during the puncture operation. Therefore, it is possible to further effectively suppress the deflection of the inner needle 16 supported by the deflection suppressing member 20.

Note that, while the configuration described above is a case in which it is configured to push the two arms 42 by the catheter operating portion 15 to open the two arms 42, it is allowable to configure to push the two arms 42 by the catheter hub 14 itself (projection provided on the catheter hub 14, etc.) to open the two arms 42.

The two arms 42 may be configured to be fitted or engaged with each other by a weak fitting force or engaging force so as not to unintentionally open in the initial state, and the two arms 42 may be configured to be released from the fitting or engaging state when pushed by the catheter operating portion 15 or the catheter hub 14, so as to open.

In the catheter assembly 10A, the configuration for detaching the catheter operating portion 15 from the deflection suppressing member 20 is not limited to the above-described configuration. Accordingly, the deflection suppressing member 20 may be configured like the deflection suppressing members 20A to 20D illustrated in FIGS. 8A to 8E, for example. The similar applies to the catheter assemblies 10B to 10D according to other embodiments described below.

Figure 8A:
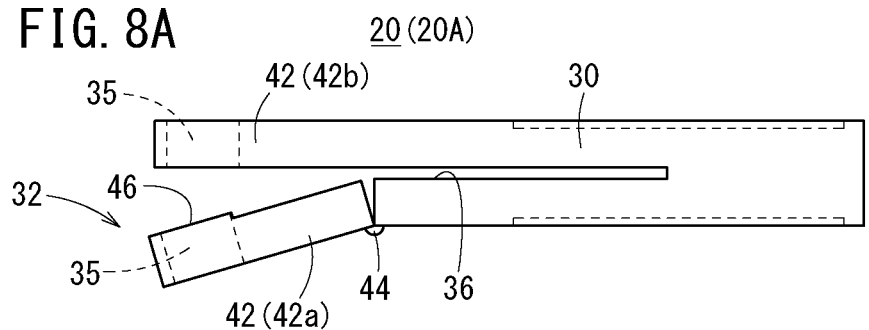
FIG. 8A is a plan view of a deflection suppressing member according to a first modification.

In the deflection suppressing member 20A illustrated in FIG. 8A, one arm 42a of the two arms 42 constituting the distal end forming portion 32 is pivotable with respect to the base portion 30 with the hinge portion 44 as a fulcrum, while the other arm 42b is integrally provided so as not to be pivotable with respect to the base portion 30.

Even with this configuration, one arm 42a is expanded when the catheter operating portion 15 moves relative to the deflection suppressing member 20A in the distal end direction, making it possible to detach the catheter operating portion 15 from the deflection suppressing member 20A. Furthermore, because the protrusion 46 is not formed on the other arm 42b, the catheter operating portion 15 can be detached from the deflection suppressing member 20A without being caught by the other arm 42b. This point is similarly applied to the cases in FIGS. 8B to 8E described below.

Figure 8B:
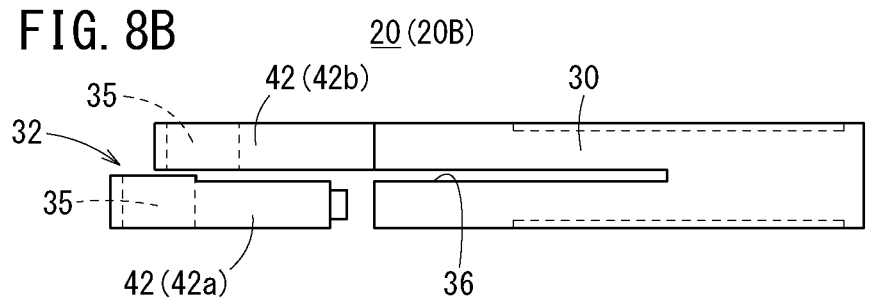
FIG. 8B is a plan view of a deflection suppressing member according to a second modification.

In the deflection suppressing member 20B illustrated in FIG. 8B, one arm 42a of the two arms 42 constituting the distal end forming portion 32 is joined, with a weak joining force (fitting force or engaging force), to the distal end of the base portion 30 in the initial state. However, when a force of a predetermined level or more is applied to the distal end direction, the one arm 42a can be separated from the distal end of the base portion 30 in the distal end direction. The other arm 42b is integrally provided so as not to be separable from the base portion 30.

Even with the configuration of FIG. 8B, when the catheter operating portion 15 moves relative to the deflection suppressing member 20B in the distal end direction, one arm 42a can be shifted in the distal end direction with respect to the base portion 30 to remove the one arm 42a, making it possible to detach the catheter operating portion 15 from the deflection suppressing member 20B.

Figure 8C:
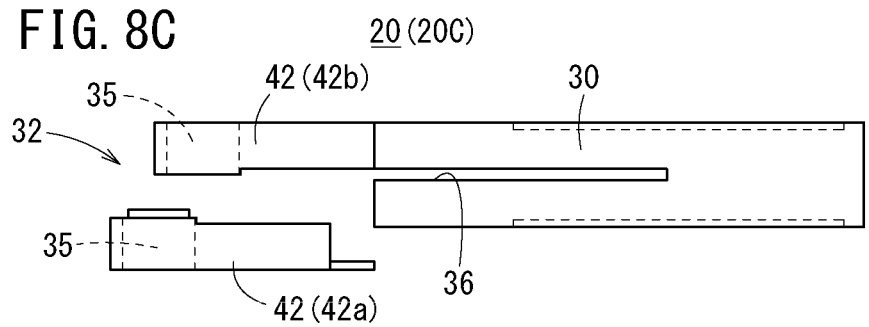
FIG. 8C is a plan view of a deflection suppressing member according to a third modification.

In the deflection suppressing member 20C illustrated in FIG. 8C, one arm 42a of the two arms 42 constituting the distal end forming portion 32 is joined to the distal end of the base portion 30 in the initial state. However, when a force of a predetermined level or more is applied toward an outer side in the width direction (arrangement direction of the two arms 42) of the deflection suppressing member 20C, the one arm 42a can be separated from the distal end of the base portion 30 toward the outer side. The other arm 42b is integrally provided so as not to be separable from the base portion 30.

Even with the configuration in FIG. 8C, one arm 42a can be shifted to the outer side in the width direction with respect to the base portion 30 so as to remove the one arm 42a when the catheter operating portion 15 moves relative to the deflection suppressing member 20C in the distal end direction, making it possible to detach the catheter operating portion 15 from the deflection suppressing member 20C. Moreover, unlike the configuration of FIG. 8B in which the force is applied in the distal end direction at separation of the arm 42a, this configuration is a case in which no force is applied in the distal end direction at separation of the arm 42a, making it possible to avoid unintentional movement of the deflection suppressing member 20C in the distal end direction. Note that the other arm 42b may be configured to be removable from the base portion 30 by being shifted in the thickness direction of the deflection suppressing member 20C with respect to the base portion 30.

Figure 8D:
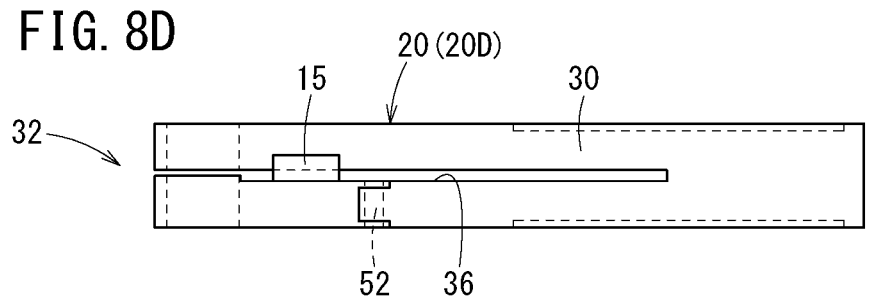
FIG. 8D is a plan view of a deflection suppressing member according to a fourth modification.
Figure 8E:
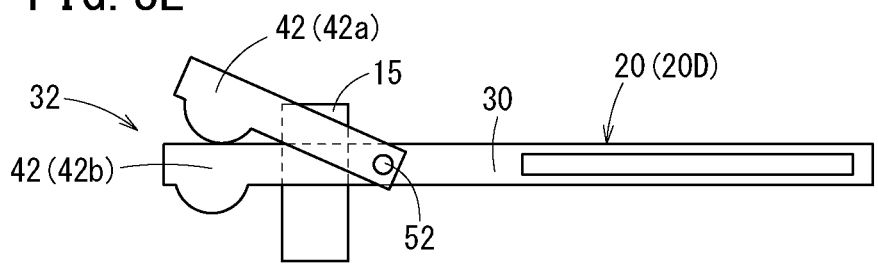
FIG. 8E is a side view of the deflection suppressing member according to the fourth modification.

In the deflection suppressing member 20D illustrated in FIG. 8D and FIG. 8E, one arm 42a of the two arms 42 constituting the distal end forming portion 32 is pivotable with respect to the base portion 30 having an axial portion 52 along the width direction of the deflection suppressing member 20D as a fulcrum. The other arm 42b is integrally provided so as not to be pivotable from the base portion 30. Even with this configuration, one arm 42a is rotated upward when the catheter operating portion 15 moves relative to the deflection suppressing member 20D in the distal end direction, making it possible to detach the catheter operating portion 15 from the deflection suppressing member 20D.

Figure 9:
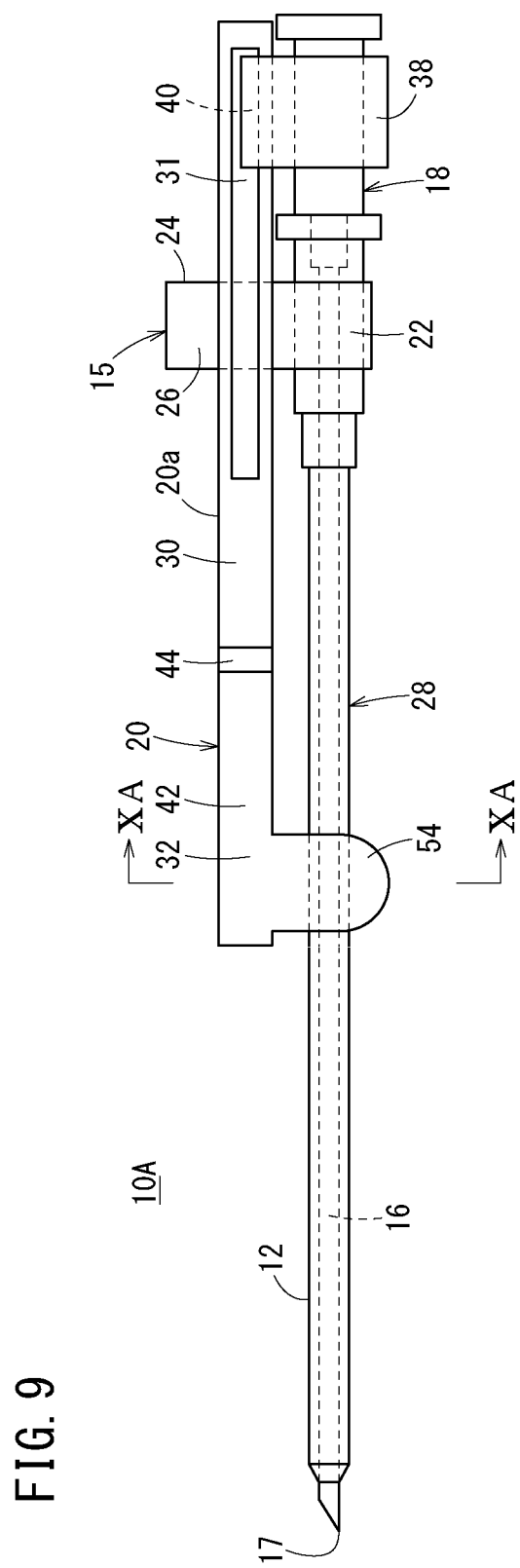
FIG. 9 is a side view of a catheter assembly having a support portion according to another configuration example.

As illustrated in FIG. 9, it is allowable in the catheter assembly 10A to adopt a support portion 54 configured to surround at least half of the outer peripheral surface of the catheter 12 in the circumferential direction, in place of the support portion 34 that supports the inner needle 16 from one direction alone. With this support portion 54, it is possible suppress deflection of the inner needle 16 also in the downward direction and the left-right direction in addition to the upward direction. The similar applies to the catheter assemblies 10B to 10D according to other embodiments described below. The support portion 54 is configured like support portions 54A to 54E respectively illustrated in FIGS. 10A to 10E, for example.

Figure 10A:
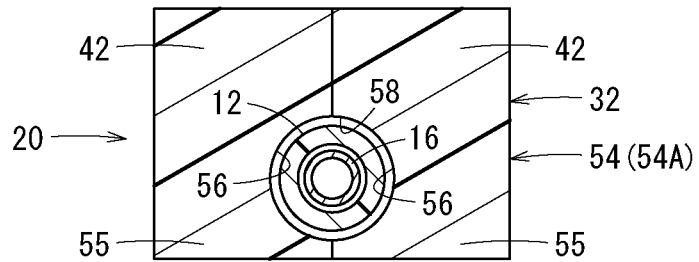
FIG. 10A is a cross-sectional view of a support portion according to a first configuration example taken along line XA-XA in FIG. 9.

The support portion 54A illustrated in FIG. 10A is configured to surround the entire circumference of the outer peripheral surface of the catheter 12. A semicircular recess 56 is formed on an inner surface of each of the two support elements 55. The two recesses 56 form a holding hole 58 penetrating along the axial direction of the inner needle 16. In the initial state, the outer peripheral surface of the catheter 12 and the inner surface of the holding hole 58 may be in contact with each other, or may be in proximity to each other via a slight gap.

Figure 10B:
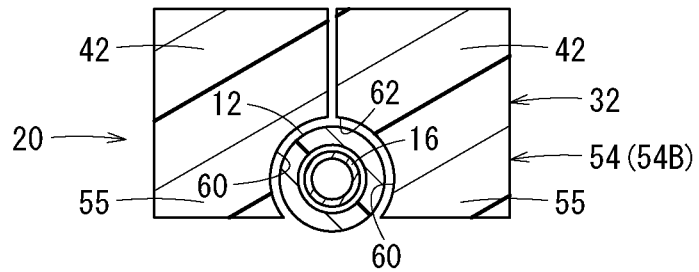
FIG. 10B is a cross-sectional view of a support portion according to a second configuration example.

The support portion 54B illustrated in FIG. 10B is configured to surround the outer peripheral surface of the catheter 12 so as to expose a portion (a range less than 180°) of the circumferential direction. An arcuate recess 60 that is less than a semicircle is formed on the inner surface of the two support elements 55. The two recesses 60 form a holding groove 62 penetrating along the axial direction of the inner needle 16. With this support portion 54B, it is possible to suppress deflection of the inner needle 16 also in the downward direction and the left-right direction in addition to the upward direction, similarly to the case of the support portion 54A.

Figure 10C:
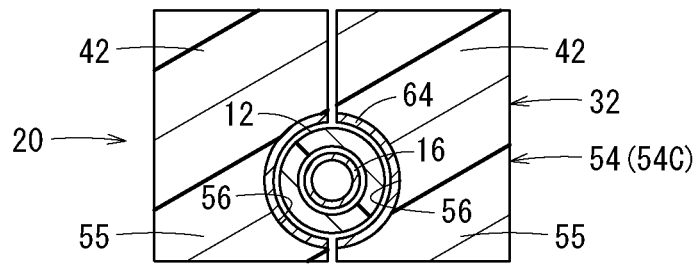
FIG. 10C is a cross-sectional view of a support portion according to a third configuration example.

The support portion 54C illustrated in FIG. 10C includes the two support elements 55 on which the recess 56 is formed similarly to the support portion 54A illustrated in FIG. 10A. On the inner surface of the recess 56, a gel material 64 is applied as a friction reduction member for reducing frictional resistance (sliding resistance) between the outer peripheral surface of the catheter 12 and the inner surface of the support portion 54C. With the configuration of FIG. 10C, even when a coating (lubricating coating) for reducing the puncture resistance is formed on the outer peripheral surface of the catheter 12, it is possible to suppress peeling of the lubricant coat at movement of the deflection suppressing member 20 relative to the catheter 12 in the axial direction.

Figure 10D:
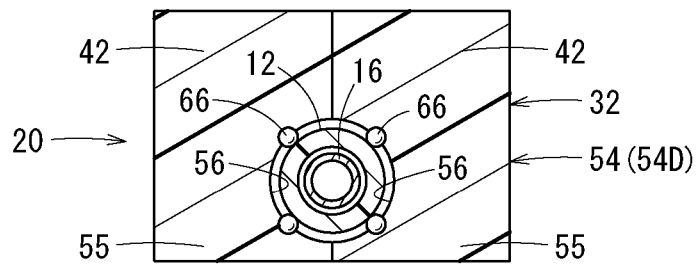
FIG. 10D is a cross-sectional view of a support portion according to a fourth configuration example.

The support portion 54D illustrated in FIG. 10D includes the two support elements 55 on which the recess 56 is formed similarly to the support portion 54A illustrated in FIG. 10A. On the inner surface of the recess 56, a plurality of (four in FIG. 10D) freely rotatable spheres 66 (rolling elements) is arranged to be spaced apart from each other in the circumferential direction as a friction reduction member for reducing the frictional resistance between the outer peripheral surface of the catheter 12 and the inner surface of the support portion 54D. These spheres 66 are in point contact with the outer peripheral surface of the catheter 12. With the configuration of FIG. 10D, even when the lubricating coating is formed on the outer peripheral surface of the catheter 12, it is possible to minimize damage occurring in the lubricating coating during movement of the deflection suppressing member 20 relative to the catheter 12 in the axial direction.

Figure 10E:
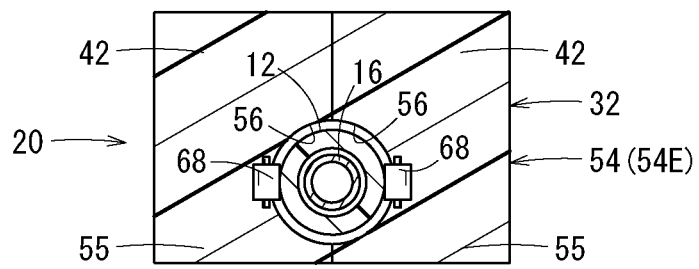
FIG. 10E is a cross-sectional view of a support portion according to a fifth configuration example.

The support portion 54E illustrated in FIG. 10E includes the two support elements 55 on which the recess 56 is formed similarly to the support portion 54A illustrated in FIG. 10A. On the inner surface of the recess 56, a plurality of (two in FIG. 10E) freely rotatable cylindrical rollers (rolling elements) 68 is arranged to be spaced apart from each other in the circumferential direction as a friction reduction member for reducing the frictional resistance between the outer peripheral surface of the catheter 12 and the inner surface of the support portion 54E. These cylindrical rollers 68 are in point contact with the outer peripheral surface of the catheter 12. With the configuration of FIG. 10E, even when the lubricating coating is formed on the outer peripheral surface of the catheter 12, it is possible to minimize damage occurring in the lubricating coating during movement of the deflection suppressing member 20 relative to the catheter 12 in the axial direction.

Second Embodiment

Figure 11A:
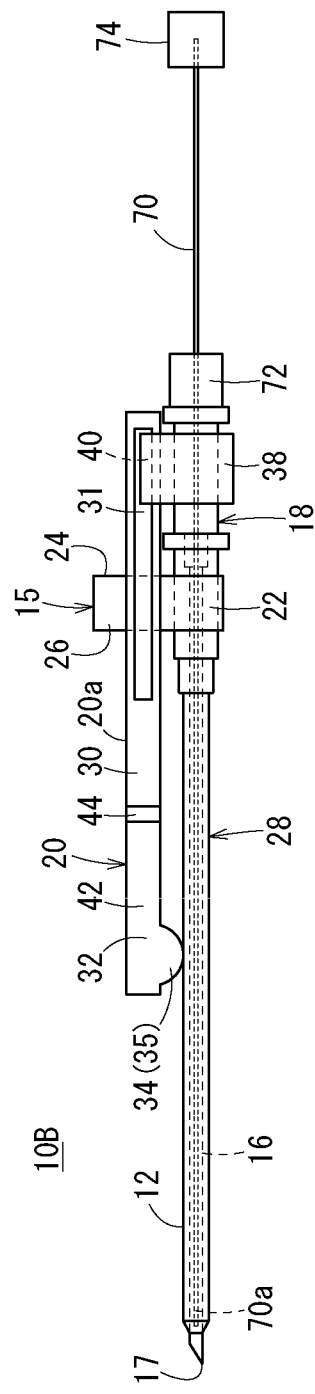
FIG. 11A is a side view of the catheter assembly according to the second embodiment.

The catheter assembly 10B according to a second embodiment illustrated in FIG. 11A is a catheter assembly 10A to which a guide wire 70 has been added. The guide wire 70 is a flexible linear member and is inserted into the inner cavity of the inner needle 16 so as to be slidable in the axial direction. The guide wire 70 is longer than the overall length of the inner needle 16 and the catheter 12 and is set to a length that can protrude from the distal end of the inner needle 16 by a predetermined length by advancing operation of the guide wire 70.

Moreover, in the catheter assembly 10B, a guide member 72 that guides the guide wire 70 and generates appropriate movement resistance to the guide wire 70 is attached to the proximal end portion of the needle hub 18. The guide member 72 also has a sealing function of preventing blood leakage from the proximal end of the needle hub 18 at the puncture into the blood vessel using the inner needle 16. A stopper 74 formed thicker than the guide wire 70 is fixed to the proximal end portion of the guide wire 70.

Figure 11B:
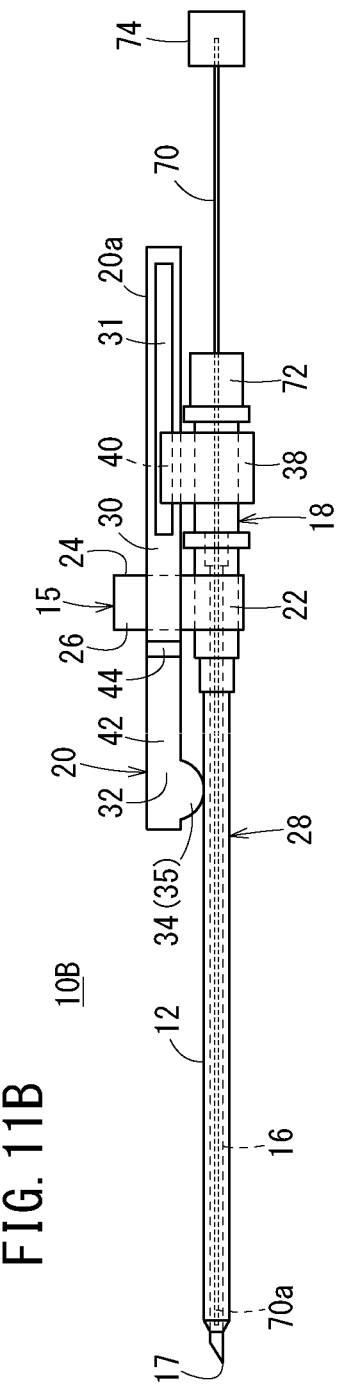
FIG. 11B is a first diagram illustrating a method of using the catheter assembly according to the second embodiment.

In application of the catheter assembly 10B, the user punctures into the blood vessel 50 with the distal end portions of the inner needle 16 and the catheter 12 similarly to the case of the catheter assembly 10A. With this configuration, as illustrated in FIG. 11B, the catheter assembly 10B shifts to a state in which members other than the deflection suppressing member 20 have moved relative to the deflection suppressing member 20 in the distal end direction. Thereafter, the guide wire 70 is used as necessary or in accordance with user's preference.

In a case in which the guide wire 70 is not to be used after the above-described puncture operation, the user operates the catheter operating portion 15 in the distal end direction while holding the position of the guide wire 70 with respect to the inner needle 16 as illustrated in FIG. 12A. With this operation, the user advances the catheter 12 with respect to the inner needle 16 and inserts the distal end portion of the catheter 12 into the blood vessel 50 by a predetermined length. The subsequent operation procedure is similar to that of the catheter assembly 10A.

In a case in which the guide wire 70 is to be used after the above-described puncture operation, the user moves the guide wire 70 in the distal end direction with respect to the inner needle 16 as illustrated in FIG. 12B so as to allow the guide wire 70 to protrude from the distal end of the inner needle 16 by a predetermined length. At this time, the stopper 74 fixed to the proximal end portion of the guide wire 70 comes into contact with the guide member 72, making it possible to prevent excessive insertion of the guide wire 70 into the blood vessel 50.

Next, as illustrated in FIG. 12C, the user operates the catheter operating portion 15 in the distal end direction to advance the catheter 12 with respect to the inner needle 16 so as to insert the distal end portion of the catheter 12 into the blood vessel 50 by a predetermined length along the outer peripheral surface of the guide wire 70 inserted beforehand. The subsequent operation procedure is similar to the case of the catheter assembly 10A.

Among the second embodiment, the same or similar functions and effects as those of the first embodiment can be obtained for portions common to the first embodiment.

Third Embodiment

Figure 13A:
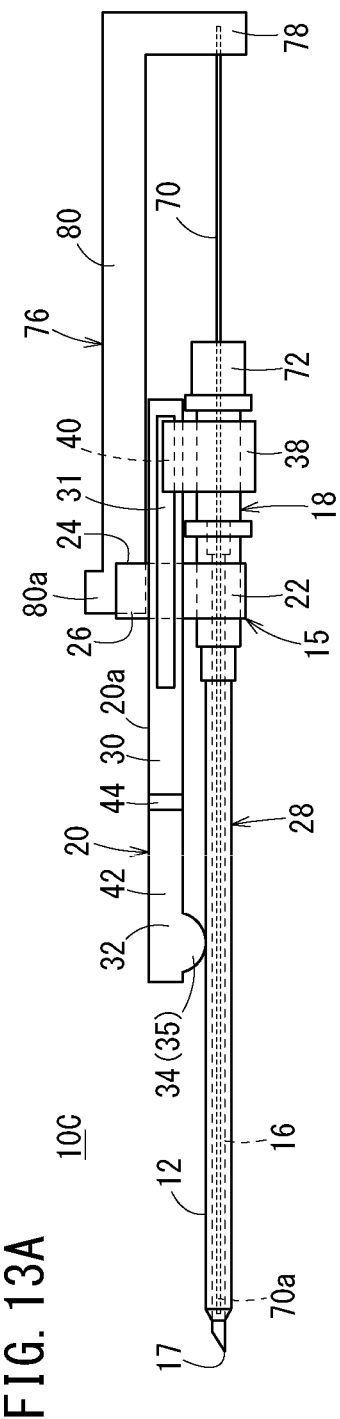
FIG. 13A is a side view of a catheter assembly according to a third embodiment.

In the catheter assembly 10C according to a third embodiment illustrated in FIG. 13A, the stopper 74 in the above-described catheter assembly 10B has substantially been replaced with a wire operating portion 76. The wire operating portion 76 includes: a wire holding portion 78 connected and fixed to the proximal end portion of the guide wire 70; and a main body portion 80 extending in the distal end direction from the upper end portion of the wire holding portion 78.

The main body portion 80 faces the upper surface 20a of the deflection suppressing member 20 in an initial state and is separably connected to the catheter operating portion 15. Specifically, the distal end portion 80a of the main body portion 80 and the operating element 26 of the catheter operating portion 15 are releasably engaged or fitted. Accordingly, when a force of a predetermined level or more is applied, the distal end portion of the main body portion 80 and the operating element 26 of the catheter operating portion 15 release the engagement or fitting so as to be separable. The distal end 70a of the guide wire 70 is arranged in the vicinity of the distal end inside the inner needle 16 in a state in which the deflection suppressing member 20 and the catheter operating portion 15 are connected to each other.

Figure 13B:
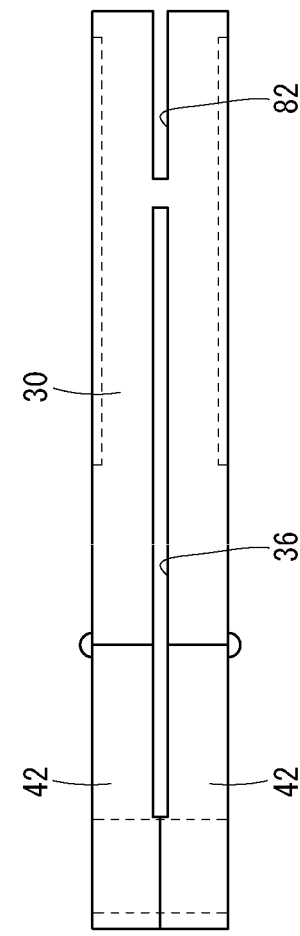
FIG. 13B is a plan view of a deflection suppressing member of the catheter assembly according to the third embodiment.

As illustrated in FIG. 13B, the proximal end portion of the deflection suppressing member 20 includes a groove portion 82 formed to extend along the longitudinal direction of the deflection suppressing member 20, opening in the proximal direction, and penetrating in the thickness direction of the deflection suppressing member 20.

Figure 14A:
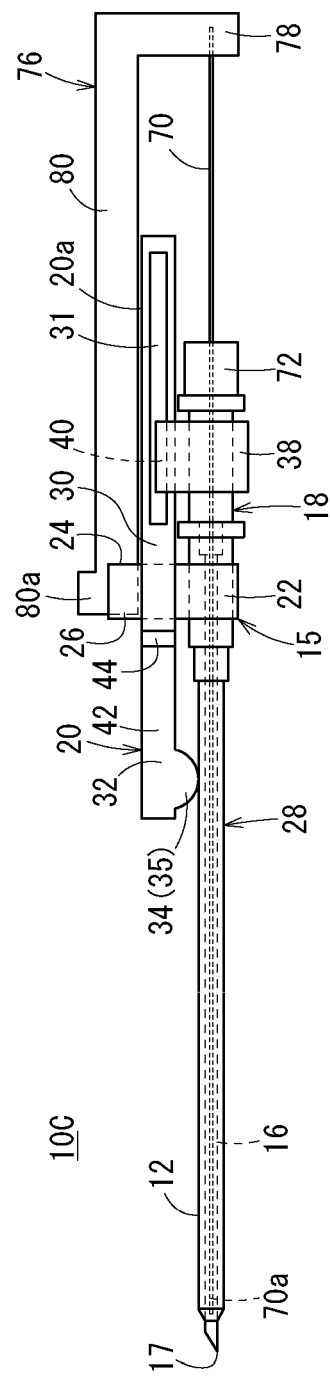
FIG. 14A is a first diagram illustrating a method of using the catheter assembly according to the third embodiment.

In application of the catheter assembly 10C, the user punctures into the blood vessel 50 with the distal end portions of the inner needle 16 and the catheter 12 similarly to the case of the catheter assembly 10A. With this configuration, as illustrated in FIG. 14A, the catheter assembly 10C shifts to a state in which members other than the deflection suppressing member 20 (for example, catheter 12) have moved relative to the deflection suppressing member 20 in the distal end direction. During puncture operation, the wire operating portion 76 and the catheter operating portion 15 are engaged or fitted with each other, so as to maintain their relative positions. As a result, the distal end position of the guide wire 70 is held in the vicinity of the distal end inside the inner needle 16.

Figure 14B:
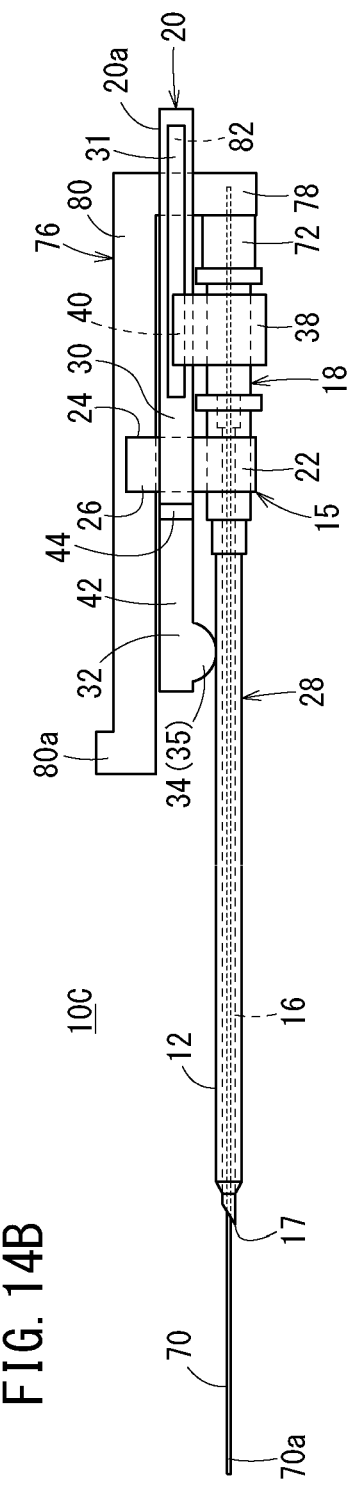
FIG. 14B is a second diagram illustrating a method of using the catheter assembly according to the third embodiment.

Next, as illustrated in FIG. 14B, the user operates the wire operating portion 76 in the distal end direction to move the guide wire 70 in the distal end direction with respect to the inner needle 16. This operation allows the guide wire 70 to protrude from the distal end of the inner needle 16 by a predetermined length. Because the distal end position of the guide wire 70 is positioned in the vicinity of the distal end inside the inner needle 16 in a state immediately before operating the wire operating portion 76 in the distal end direction, the guide wire 70 is promptly inserted into the blood vessel 50 with advance of the guide wire 70.

Furthermore, in a state immediately before operating the wire operating portion 76 in the distal end direction, the distal end portion of the wire operating portion 76 is in contact with the operating element 26 of the catheter operating portion 15, and both are at substantially the same position. With this configuration, the distal end portion of the wire operating portion 76 can be operated with the same hand as the hand operating the operating element 26 of the catheter operating portion 15, leading to excellent operability.

The advancing operation of the wire operating portion 76 allows the wire operating portion 76 to enter the inside of the groove portion 82 formed at the proximal end portion of the deflection suppressing member 20. With this operation, it is possible to avoid the interference between the wire operating portion 76 and the deflection suppressing member 20, achieving the advancing operation of the wire operating portion 76 without any problem.

Figure 15:
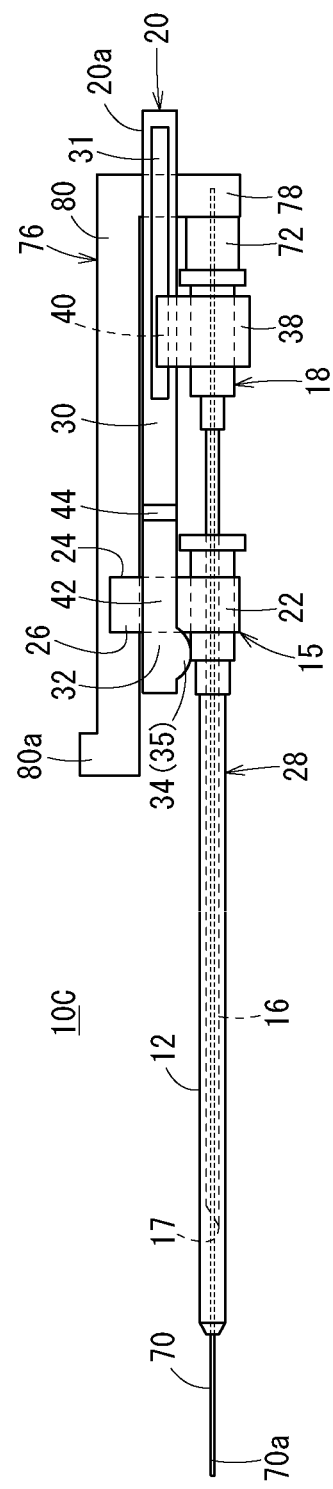
FIG. 15 is a third diagram illustrating a method of using the catheter assembly according to the third embodiment.

Next, as illustrated in FIG. 15, the user operates the catheter operating portion 15 in the distal end direction to advance the catheter 12 with respect to the inner needle 16 so as to insert the distal end portion of the catheter 12 into the blood vessel 50 by a predetermined length along the outer peripheral surface of the guide wire 70 inserted beforehand. The subsequent operation procedure is similar to the case of the catheter assembly 10A.

As illustrated in FIGS. 16A to 16C, the guide wire 70 exposed to the outside of the needle hub 18 may be folded back at a guide portion 84 so as to allow the end portion 70b (end portion on the opposite side to the side to be inserted into the blood vessel 50) to be fixed to the needle hub 18 or to another member fixed to the needle hub 18. The guide portion 84 is supported by the proximal end portion of the wire operating portion 76. The guide portion 84 may be in the form of a rotatable guide roller or may have a non-rotating form.

In FIG. 16A, the end portion 70b of the guide wire 70 is fixed to the needle hub 18. In FIG. 16B, the end portion 70b of the guide wire 70 is fixed to the guide member 72. In FIG. 16C, the end portion 70b of the guide wire 70 is fixed to the slide support body 38.

When the wire operating portion 76 is operated in the distal end direction with respect to the inner needle 16 and the needle hub 18 in application of the catheter assembly 10C illustrated in FIGS. 16A to 16C, the guide wire 70 (portion wound around the guide portion 84) is pushed in the distal end direction by the proximal end portion of the wire operating portion 76. With this operation, the portion of the guide wire 70 on the side inserted into the inner needle 16 (portion from the distal end of the guide wire 70 to the guide portion 84) moves in the distal end direction with respect to the inner needle 16. The moving distance of the guide wire 70 with respect to the inner needle 16 at this time is twice the moving distance of the wire operating portion 76. Accordingly, the guide wire 70 can be advanced by a predetermined distance with a shorter operation length.

Among the third embodiment, the same or similar functions and effects as those of the first embodiment can be obtained for portions common to the first embodiment.

Fourth Embodiment

Figure 17A:
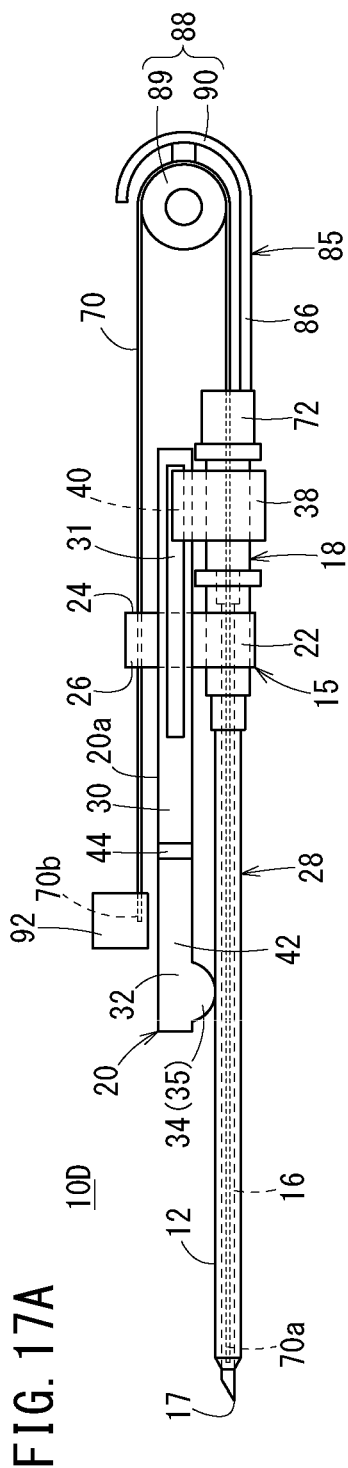
FIG. 17A is a side view of a catheter assembly according to a fourth embodiment.

The catheter assembly 10D according to the fourth embodiment illustrated in FIG. 17A includes a folding mechanism 85 that folds the guide wire 70 extending from the needle hub 18 in the distal end direction. The folding mechanism 85 includes: a frame 86 fixed to the guide member 72 and extending in the proximal direction; and a guide portion 88 provided at the proximal end portion of the frame 86. Note that the frame 86 may be fixed to the needle hub 18 or may be fixed to the slide support body 38.

The guide portion 88 includes an inner guide 89 and an outer guide 90. The inner guide 89 may be in the form of a rotatable guide roller or may have a non-rotating form. The outer guide 90 extends from the proximal end of the frame 86 so as to be curved in an arc shape. A wire operating portion 92 is fixed to the end portion 70b of the guide wire 70.

Figure 17B:
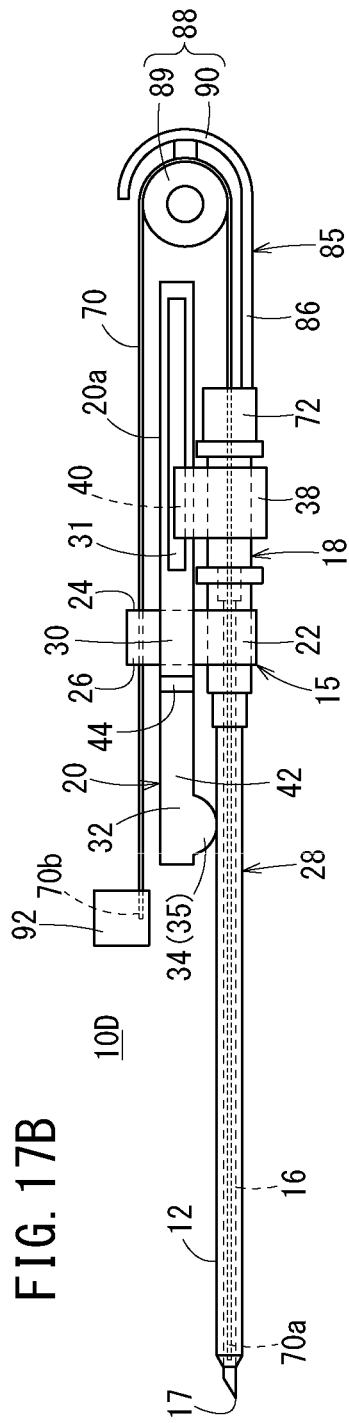
FIG. 17B is a first diagram illustrating a method of using the catheter assembly according to a fourth embodiment.

In application of the catheter assembly 10D, the user punctures into the blood vessel 50 with the distal end portions of the inner needle 16 and the catheter 12 similarly to the case of the catheter assembly 10A. With this configuration, as illustrated in FIG. 17B, the catheter assembly 10D shifts to a state in which members other than the deflection suppressing member 20 (for example, catheter 12) have moved relative to the deflection suppressing member 20 in the distal end direction.

Next, as illustrated in FIG. 18A, when the user operates the wire operating portion 92 in the proximal end direction with respect to the inner needle 16 and the needle hub 18, the guide wire 70 is guided slidably in the guide portion 88, and together with this, a portion of the guide wire 70 on the side inserted into the needle 16 (portion from the distal end of the guide wire 70 to the guide portion 88) moves in the distal end direction with respect to the inner needle 16. This operation allows the guide wire 70 to move in the distal wend direction with respect to the inner needle 16 and allows the guide wire 70 to protrude from the distal end of the inner needle 16 by a predetermined length.

Next, as illustrated in FIG. 18B, the user operates the catheter operating portion 15 in the distal end direction to advance the catheter 12 with respect to the inner needle 16 so as to insert the distal end portion of the catheter 12 into the blood vessel 50 by a predetermined length along the outer peripheral surface of the guide wire 70 inserted beforehand. The subsequent operation procedure is similar to the case of the catheter assembly 10A.

Among the fourth embodiment, the same or similar functions and effects as those of the first embodiment can be obtained for portions common to the first embodiment.

The present invention is not limited to the above-described embodiment, and various modifications are possible without departing from the scope and spirit of the present invention.

What is claimed is:
1. A catheter assembly comprising:
a catheter;
a catheter hub connected to the catheter;
an inner needle removably disposed in the catheter;
a needle hub connected to the inner needle; and
a deflection suppressing member that suppresses deflection of the inner needle by supporting the inner needle via the catheter at a location distal of the catheter hub,
wherein the deflection suppressing member is supported so as to be movable relative to the needle hub and the catheter in an axial direction,
wherein the deflection suppressing member includes, at a distal end thereof, a support portion that contacts the catheter and that is movable relative to the catheter while maintaining contact with the catheter, and
wherein the catheter assembly is configured such that at least the needle hub and the catheter are advanceable together relative to the deflection suppressing member.
2. The catheter assembly according to claim 1,
wherein the catheter includes:
a first outer peripheral surface facing the deflection suppressing member; and
a second outer peripheral surface opposite the first outer peripheral surface in a radial direction,
wherein the support portion is supported so as to contact only the first outer peripheral surface of the catheter.
3. The catheter assembly according to claim 1,
wherein the support portion is supported so as to be movable relative to the needle hub in the axial direction while maintaining contact with the catheter.
4. The catheter assembly according to claim 1, wherein:
the needle hub includes a guide projection,
the deflection suppressing member includes at least one groove configured to engage with the guide projection of the needle hub, and
a length of the groove is longer than ½ of an overall length of the catheter.
5. The catheter assembly according to claim 4,
wherein the at least one groove includes:
a first groove formed at a first outer side surface of the deflection suppressing member; and
a second groove formed at a second outer side surface of the deflection suppressing member.
6. The catheter assembly according to claim 1, wherein:
the inner needle is hollow and has an inner cavity, and
the catheter assembly further comprises a guide wire disposed in the inner cavity so as to be movable relative to the inner needle in the axial direction.
7. The catheter assembly according to claim 6, further comprising:
a wire operating portion that supports the guide wire; and
a catheter operating portion disposed on the catheter hub,
wherein the catheter operating portion includes an operating element protruding from a side of the deflection suppressing member opposite the catheter hub, and a distal end portion of the wire operating portion is in contact with or in proximity to the operating element of the catheter operating portion in an initial state of the catheter assembly.

8. The catheter assembly according to claim 1, wherein:
the support portion is in contact with an outer peripheral surface of the catheter and surrounds at least half of the outer peripheral surface of the catheter in a circumferential direction.

9. The catheter assembly according to claim 8, further comprising:
a friction reduction member configured to reduce frictional resistance between the support portion and the catheter, the friction reduction member being disposed on an inner peripheral portion of the support portion.

10. The catheter assembly according to claim 9, wherein:
the friction reduction member is a gel material or a rolling element that contacts the catheter.

11. The catheter assembly according to claim 1, further comprising:
a catheter operating portion disposed on the catheter hub, wherein the deflection suppressing member includes a slit permitting relative movement of the catheter operating portion in the axial direction,
wherein the catheter operating portion protrudes from a side of the deflection suppressing member opposite the catheter hub via the slit in the deflection suppressing member.

12. The catheter assembly according to claim 11, wherein:
the catheter operating portion includes an engaging portion configured to engage with the deflection suppressing member so as to suppress deflection of the deflection suppressing member.

13. The catheter assembly according to claim 11,
wherein the deflection suppressing member includes:
a base portion supported by the needle hub and extending in the axial direction; and
a distal end forming portion extending from the base portion in a distal end direction and enabling detachment of the catheter operating portion from the slit.

14. The catheter assembly according to claim 13, wherein:
the distal end forming portion includes two arms that closes a distal end of the slit in an initial state, and
at least one arm of the two arms is movable with respect to the base portion.

15. The catheter assembly according to claim 14, wherein:
the at least one arm is pivotable with respect to the base portion via a hinge portion.

16. The catheter assembly according to claim 14, wherein:
the at least one arm is detachable from the base portion.

17. A method of using a catheter assembly, the method comprising:
providing the catheter assembly, which comprises:
a catheter,
a catheter hub connected to the catheter,
an inner needle removably disposed in the catheter,
a needle hub connected to the inner needle, and
a deflection suppressing member that suppresses deflection of the inner needle by supporting the inner needle via the catheter at a location distal of the catheter hub,
wherein the deflection suppressing member is supported so as to be movable relative to the needle hub and the catheter in an axial direction,
wherein the deflection suppressing member includes, at a distal end thereof, a support portion that contacts the catheter and that is movable relative to the catheter while maintaining contact with the catheter;
grasping the catheter assembly and puncturing skin of a patient toward a blood vessel of the patient with the inner needle and the catheter; and
puncturing the blood vessel with a distal end of each of the inner needle and the catheter by advancing at least the needle hub and the catheter relative to the deflection suppressing member while holding the deflection suppressing member.

18. A catheter assembly comprising:
a catheter;
a catheter hub connected to the catheter;
an inner needle removably disposed in the catheter;
a needle hub connected to the inner needle; and
a deflection suppressing member that suppresses deflection of the inner needle by supporting the inner needle via the catheter at a location distal of the catheter hub,
wherein the deflection suppressing member is supported so as to be movable relative to the needle hub and the catheter in an axial direction,
wherein the deflection suppressing member includes, at a distal end thereof, a support portion that contacts the catheter and that is movable relative to the catheter while maintaining contact with the catheter,
wherein the inner needle is hollow and has an inner cavity, and
wherein the catheter assembly further comprises a guide wire disposed in the inner cavity so as to be movable relative to the inner needle in the axial direction.

19. The catheter assembly according to claim 18, further comprising:
a wire operating portion that supports the guide wire; and
a catheter operating portion disposed on the catheter hub,
wherein the catheter operating portion includes an operating element protruding from a side of the deflection suppressing member opposite the catheter hub, and
a distal end portion of the wire operating portion is in contact with or in proximity to the operating element of the catheter operating portion in an initial state of the catheter assembly.

* * * * *